United States Patent
Chen et al.

(10) Patent No.: US 9,730,975 B2
(45) Date of Patent: Aug. 15, 2017

(54) CHEMICAL REPROGRAMMING OF HUMAN GLIAL CELLS INTO NEURONS FOR BRAIN AND SPINAL CORD REPAIR

(71) Applicant: THE PENN STATE RESEARCH FOUNDATION, University Park, PA (US)

(72) Inventors: Gong Chen, State College, PA (US); Gang-Yi Wu, State College, PA (US); Lei Zhang, State College, PA (US); Jiu-Chao Yin, State College, PA (US); Hana Yeh, State College, PA (US); Ning-Xin Ma, State College, PA (US); Grace Lee, State College, PA (US)

(73) Assignee: The Penn State Research Foundation, University Park, PA (US)

( * ) Notice: Subject to any disclaimer, the term of this patent is extended or adjusted under 35 U.S.C. 154(b) by 0 days.

(21) Appl. No.: 14/951,723

(22) Filed: Nov. 25, 2015

(65) Prior Publication Data

US 2016/0143984 A1   May 26, 2016

Related U.S. Application Data

(60) Provisional application No. 62/084,365, filed on Nov. 25, 2014, provisional application No. 62/215,828, filed on Sep. 9, 2015.

(51) Int. Cl.
```
A61K 38/05      (2006.01)
A61K 31/00      (2006.01)
C12N 5/079      (2010.01)
C12N 5/0793     (2010.01)
A61K 31/519     (2006.01)
A61K 31/4439    (2006.01)
A61K 31/506     (2006.01)
```
(52) U.S. Cl.
CPC .............. *A61K 38/05* (2013.01); *A61K 31/00* (2013.01); *A61K 31/4439* (2013.01); *A61K 31/506* (2013.01); *A61K 31/519* (2013.01); *C12N 5/0619* (2013.01); *C12N 2501/15* (2013.01); *C12N 2501/155* (2013.01); *C12N 2501/727* (2013.01); *C12N 2501/998* (2013.01); *C12N 2501/999* (2013.01); *C12N 2506/08* (2013.01)

(58) Field of Classification Search
None
See application file for complete search history.

(56) References Cited

U.S. PATENT DOCUMENTS

| 8,642,334 B2 | 2/2014 | Chambers et al. |
| 8,669,048 B2 | 3/2014 | Pera et al. |
| 2009/0098093 A1 | 4/2009 | Edge |
| 2011/0086379 A1 | 4/2011 | Blak et al. |
| 2011/0091927 A1 | 4/2011 | Reubinoff |
| 2011/0250684 A1 | 10/2011 | Akamatsu et al. |
| 2012/0108507 A1 | 5/2012 | Zhu et al. |
| 2012/0142093 A1 | 6/2012 | Takahashi et al. |
| 2012/0207744 A1 | 8/2012 | Mendlein et al. |
| 2012/0220034 A1 | 8/2012 | Ahlfors et al. |
| 2012/0277111 A1 | 11/2012 | Crabtree |
| 2012/0288936 A1 | 11/2012 | Ahlfors et al. |
| 2013/0183674 A1 | 7/2013 | Studer et al. |
| 2013/0202649 A1 | 8/2013 | Cooke et al. |
| 2014/0038291 A1 | 2/2014 | Ahlfors |
| 2014/0193341 A1 | 7/2014 | Abeliovich et al. |

FOREIGN PATENT DOCUMENTS

| EP | 2614829 | 7/2013 |
| WO | 2010063848 | 6/2010 |
| WO | 2010068758 | 6/2010 |
| WO | 2010108005 | 9/2010 |
| WO | 2013011093 | 1/2013 |
| WO | 2013086570 | 6/2013 |
| WO | 2013163455 | 10/2013 |
| WO | 2014125481 | 8/2014 |

OTHER PUBLICATIONS

Borghese et al., Stem Cells, 28:955-964, 2010.*
Ladewig et al., Nature Methods, 9(6):575-578, published online Apr. 8, 2012.*
Niu et al., Nature Cell Biology, 15(10): 1164-74, published online Sep. 22, 2013.*
Chen et al., Specification of Region-Specific Neurons Including Forebrain Glutamatergic Neurons from Human Induced Pluripotent Stem Cells, PLoS One, Jul. 2010, vol. 5, Iss. 7, e11853. Jul. 29, 2010.

* cited by examiner

Primary Examiner — Kimberly A. Ballard
Assistant Examiner — Stacey MacFarlane
(74) Attorney, Agent, or Firm — Hodgson Russ LLP

(57) ABSTRACT

Provided are methods and compositions from reprogramming human glial cells into human neurons. The reprogramming is achieved using combinations of compounds that can modify signaling via Transforming growth factor beta (TGF-β), Bone morphogenetic protein (BMP), glycogen synthase kinase 3 (GSK-3), and γ-secretase/Notch pathways. The reprogramming is demonstrated using groups of three or four compounds that are chosen from the group thiazovivin, LDN193189, SB431542, TTNPB, CHIR99021, DAPT, VPA, SAG, purmorphamine. Reprogramming is demonstrated using the group of LDN193189/CHIR99021/DAPT, the group of B431542/CHIR99021/DAPT, the group of LDN193189/DAPT/SB431542, the group of LDN193189/CHIR99021/SB431542, a three drug combination of SB431542/CHIR99021/DAPT. Reprogramming using functional analogs of the compounds is also provided, as are pharmaceutical formulations that contain the drug combinations.

4 Claims, 19 Drawing Sheets
(14 of 19 Drawing Sheet(s) Filed in Color)

CHEMICAL REPROGRAMMING OF HUMAN GLIAL CELLS INTO NEURONS FOR BRAIN AND SPINAL CORD REPAIR

CROSS REFERENCE TO RELATED APPLICATIONS

This application claims priority to U.S. provisional application No. 62/084,365, filed Nov. 25, 2014, and to U.S. provisional application No. 62/215,828, filed Sep. 9, 2015, the disclosures of each of which are incorporated herein by reference.

STATEMENT REGARDING FEDERALLY SPONSORED RESEARCH

This invention was made with government support under contract no. MH083911 and AG045656 awarded by the National Institutes of Health. The government has certain rights in the invention.

FIELD

The present disclosure relates generally to prophylaxis and therapy of conditions related to glial scar tissue and more specifically to compositions and methods comprising small molecules for converting internal glial cells into functional neurons for brain and spinal cord repair.

BACKGROUND

Regeneration of functional neurons in neurodegenerative disorders or after nerve injury remains a major challenge in the neural repair field. Current efforts largely focus on cell replacement therapy using exogenous cells derived from embryonic stem cells or induced pluripotent stem cells (Buhnemann et al., 2006; Emborg et al., 2013; Nagai et al., 2010; Nakamura and Okano, 2013; Oki et al., 2012; Sahni and Kessler, 2010). Despite great potential, such cell transplantation approaches face significant hurdles in clinical applications such as potential immunorejection, tumorigenesis and differentiation uncertainty (Lee et al., 2013; Liu et al., 2013b; Lukovic et al., 2014). Further, while previous studies have shown that astroglial cells can be directly converted into functional neurons both in vitro (Guo et al., 2014; Heinrich et al., 2010) and in vivo (Grande et al., 2013; Torper et al., 2013; Guo et al., 2014), and that astrocytes can be converted into neuroblast cells and then differentiated into neuronal cells in stab-injured mouse brain (Niu et al., 2013) or spinal cord (Su et al., 2014), these approaches have the significant disadvantages of requiring viral infection inside the brain. Thus, such previous methodologies entail performing sophisticated brain surgery, intracranial injection of viral particles, and the considerable risk that is concomitant with such procedures. There is accordingly an ongoing and unmet need for new compositions and methods for regenerating functional neurons in the central or peripheral nervous system without the requirement for introducing exogenously reprogrammed cells or viral constructs into human subjects.

SUMMARY

The present disclosure provides compositions and methods for chemical reprogramming glial cells into neurons. The disclosure differs greatly from previous approaches, at least in part because it involves reprogramming of glial cells using chemically synthesized compounds. As such it does not include the risks associated with introducing exogenous genes, viral vectors, or engineered cells into patients, nor does it require manipulating stem cells or other multipotent cells or somatic cells such as fibroblast cells in culture to differentiate or trans-differentiate them into neurons or otherwise prepare the cells for administration to a subject. Instead, the instant disclosure encompasses reprogramming glial cells already present in the nervous system of an individual such that they are converted into neurons using combinations of small molecules that are more fully described below. The compositions and methods are expected to provide a convenient and safe approach to treat a variety of nerve injuries or neurodegenerative disorders that involve, for example, reactive glial cells or glial scars. It will be recognized by those skilled in the art that glial scars can result from a number of causes that are known in the art, and which typically involve astrogliosis after injury or disease processes in the central nervous system including brain and spinal cord, and peripheral nervous system. Reactive astrocytes are the main cellular component of glial scars, followed by NG2 glia and microglia. Thus, in embodiments, the present disclosure comprises converting astrocytes into neurons by chemically induced reprogramming of the astrocytes. But similar chemical reprogramming methods may also be used to convert NG2 glia or microglia or other cells types surrounding brain blood vessels into neurons.

As will be evident from the description, figures and data presented in this disclosure, we have developed both in vitro and in vivo data demonstrating reprogramming of preexisting, differentiated glial cells into neurons. In particular, our data demonstrate that sequential application of small molecules as described herein results in the reprogramming of the majority of human astrocytes (~70%) into neuronal cells in vitro. Further, these small molecule-reprogrammed human neurons can survive for more than five months in culture and display robust synaptic activities. Further still, injecting the human astrocyte-converted neurons into the mouse brain demonstrates that the human neurons can integrate into the local brain circuits. Thus, data presented in this disclosure collectively demonstrate that chemical reprogramming of human astrocytes into functional neurons in vivo in injured or diseased brains can now be achieved without the need to introduce into an individual cultured cells, or viral or other expression vectors or exogenous genes, which is an approach that has never before been available.

The disclosure includes the demonstration that combining compounds that together act on signaling including but not limited to the Transforming growth factor beta (TGF-β), Bone morphogenetic protein (BMP), glycogen synthase kinase 3 (GSK-3), and γ-secretase/Notch pathways can reprogram glial cells into neurons. In general, the disclosure comprises administering to an individual in need compounds that can inhibit these pathways. In one embodiment, the disclosure comprises administering a combination of compounds selected from the group consisting of thiazovivin, LDN193189, SB431542, TTNPB, CHIR99021, DAPT, VPA, SAG, purmorphamine, or pharmaceutically acceptable salts thereof, or analogs of these compounds, or compounds which have the same or similar functional effects such that their administration reprograms glial cells into neurons, and combinations of the foregoing compounds. In one approach, the compounds administered to the individual comprise at least three compounds selected from a core of four compounds that, without intending to be constrained by any particular theory, are considered to be necessary to achieve the reprogramming. These compounds are SB431542, LDN193189, CHIR 99021, and DAPT, which can also be substituted using functional analogs as described below. In one approach, the disclosure comprises using any of the following combinations: i) LDN193189/CHIR99021/DAPT, ii) SB431542/CHIR99021/DAPT; iii) LDN193189/DAPT/SB431542, and iv) LDN193189/CHIR99021/SB431542. In one embodiment, a three-drug combination of SB431542/CHIR99021/DAPT is used.

The compositions can be administered to an individual in need in any combination, and can include concurrent administration of combinations of at least two of the compounds, and can include sequential administration of any of the compounds and combinations thereof, specific embodiments of which are more fully described below. In certain approaches, a composition comprising LDN193189 and SB431542 is introduced to the individual, which may be performed as an initial administration, and a composition comprising CHIR99021 and DAPT are introduced to the individual, which may be performed in a subsequent administration.

The compositions can be administered using any acceptable route and formulations, including but not necessarily limited to oral, intranasal, intravenous and intracranial methods. In one aspect the compositions are administered orally.

In certain embodiments the method of the disclosure is used for therapeutic purposes to induce reprogramming of glial cells into neurons in an individual who is in need of the neurons due to a condition that comprises neuronal loss and/or glial scarring. In certain embodiments the individual is in need of the generated neurons due to ischemic brain damage as a consequence of stroke, hypoxia or other brain trauma, or has been diagnosed with or is suspected of having Alzheimer's disease or other neurodegenerative condition.

In another aspect the disclosure includes a pharmaceutical composition comprising a combination of at least two of thiazovivin, LDN193189, SB431542, TTNPB, CHIR99021, DAPT, VPA, SAG, purmorphamine, wherein the composition is for use of reprogramming glial cells into neurons. Pharmaceutical compositions comprising salts and analogs of these compounds, as well as functionally related compounds (i.e., functional analogs), are also contemplated. In embodiments, a pharmaceutical composition of this disclosure comprises at least two of SB431542, LDN193189, CHIR 99021, and DAPT, and/or pharmaceutically acceptable salts thereof. In embodiments the pharmaceutical composition comprises all of the SB431542, LDN193189, CHIR 99021, and DAPT, and can further comprise additional compounds. In embodiments, the disclosure includes compositions comprising as the active agents for reprogramming glial cells into neurons one of the groups: i) LDN193189/CHIR99021/DAPT, ii) SB431542/CHIR99021/DAPT, iii) LDN193189/DAPT/SB431542, and iv) LDN193189/CHIR99021/SB431542. In an embodiment, any three members of the foregoing groups are included. In one embodiment, the composition comprises or consists of a three-drug combination of SB431542/CHIR99021/DAPT.

In another aspect the disclosure includes an article of manufacture comprising packaging and at least one container, the container comprising a pharmaceutical composition comprising a combination of at least three compounds selected from the group consisting of thiazovivin, LDN193189, SB431542, TTNPB, CHIR99021, DAPT, VPA, SAG, purmorphamine, and pharmaceutically acceptable salts thereof, the packaging comprising printed information, the printed information providing an indication that the pharmaceutical composition is for use in treating a condition, wherein the condition is related to a lack of functional neurons.

BRIEF DESCRIPTION OF THE FIGURES

The patent or application file contains at least one drawing executed in color. Copies of this patent or patent application publication with the color drawings will be provided by the Office upon request and payment of the necessary fee.

Figure 3:
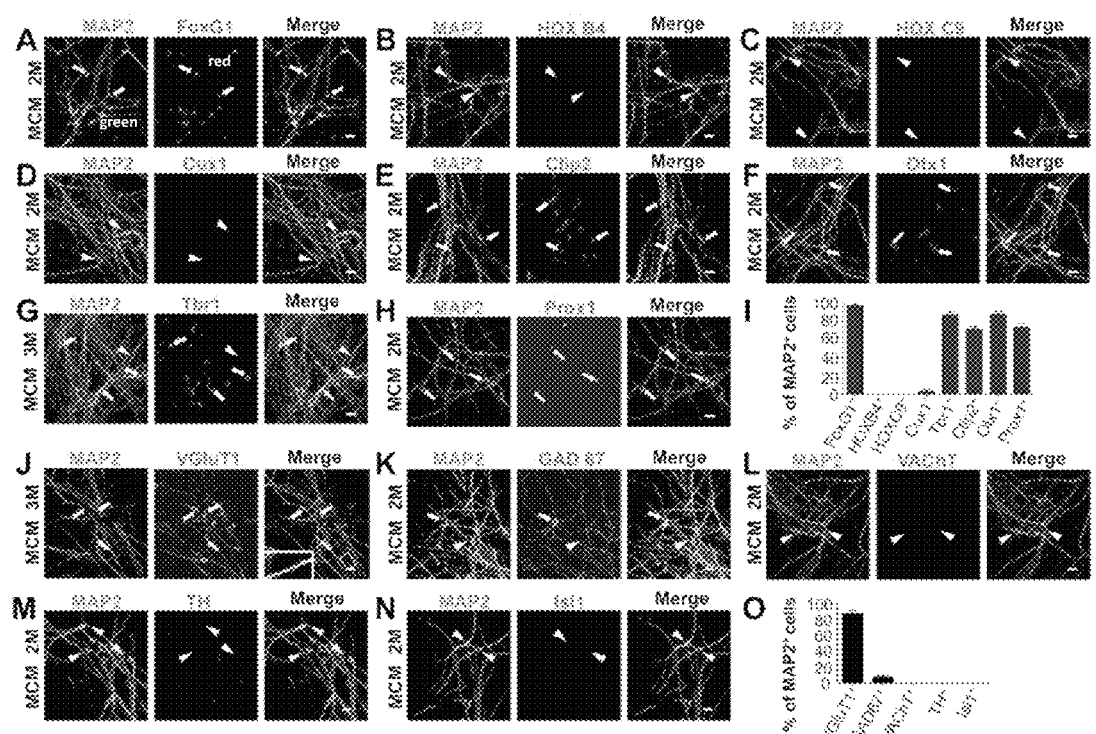

FIG. 3. Characterization of the human astrocyte-converted neurons induced by small molecules. (A-C) Immunostaining with anterior-posterior neuronal markers revealed that the small molecule-converted human neurons were positive for forebrain marker FoxG1 (A), but negative for hindbrain and spinal cord marker HOX B4 (B) and HOX C9 (C). (D-F) Immunostaining with cortical neuron markers revealed that small molecule-induced human neurons were negative for superficial layer marker Cux1 (D), but positive for deep layer marker Ctip2 (E) and Otx1 (F). (G-H) The small molecule-converted human neurons were also immunopositive for general cortical neuron marker Tbr1 (G) and hippocampal neuron marker Prox1 (H). (I) Quantitative analyses of small molecule-induced human neurons (FoxG1, 97.1±1.1%, n=3 batches; Cux1, 3.1±1.9%, n=4 batches; Ctip2, 71.4±3%, n=4 batches; Otx1, 87.4±3.2%, n=3 batches; Tbr1, 86.4±3.4%, n=3 batches; Prox1, 73.4±4.4%, n=4 batches). Scale bars: 20 µm. (J) MCM-converted human neurons were immunopositive for VGluT1. (K) A small portion of MCM-converted human neurons were GAD67-positive. (L-N) MCM-converted neurons were immunonegative for cholinergic neuronal marker vesicular acetylcholine transporter (VAChT) (L), dopaminergic neuronal marker tyrosine hydroxylase (TH) (M), or spinal motor neuron marker Isl1 (N). (O) Quantitative analyses of small molecule converted human neurons (VGluT1, 88.3±4%, n=4 batches; GAD67, 8.2±1.5%, n=4 batches). Scale bars: 20 µm. Data are represented as mean±SEM.

Figure 4:
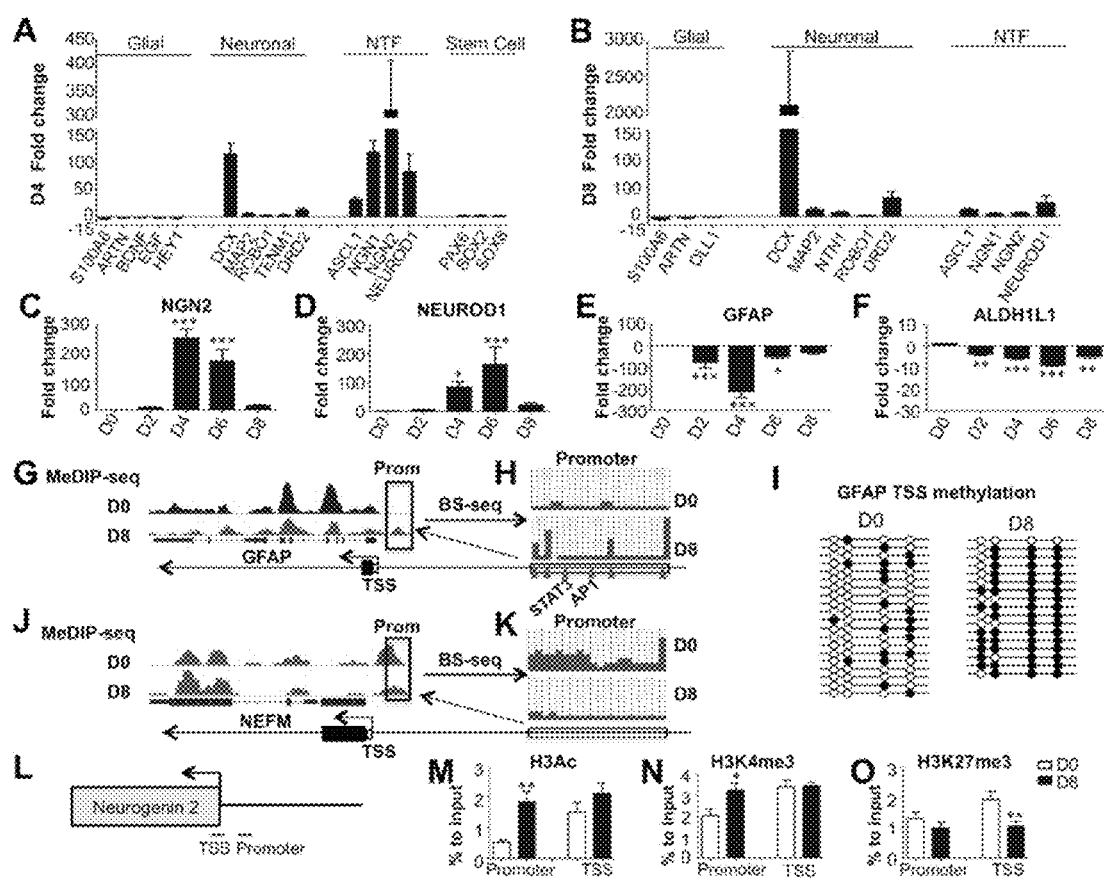

FIG. 4. Transcriptional and epigenetic regulation during chemical reprogramming of human astrocytes into neurons (A-B) PCR array revealed substantial transcriptional activation of neural transcription factors (NGN1/2, NEUROD1, and ASCL1) and immature neuronal gene DCX at day 4 (A) or day 8 (B) after small molecule treatment. Note that DCX increased >2000-fold at D8 compared to the control. The genes showing significant change in PCR array assay were presented ($P<0.05$, Mann-Whitney t test). (C-F) The time course of transcriptional changes revealed by quantitative real-time PCR analyses. Neural transcriptional factors NGN2 (C) and NEUROD1 (D) showed a peak transcription at D4 and D6, respectively; whereas astroglial genes GFAP (E) and ALDH1L1 (F) were significantly downregulated. *$P<0.05$, $P<0.01$, *$P<0.001$; Two-way ANOVA followed with Dunnett's test. N=3 batches. (G-I) Epigenetic regulation of GFAP promoter and transcription start site during chemical reprogramming MeDIP-seq revealed a significant increase of methylation in the GFAP promoter region (G, box region) after 8 days of small molecule treatment, which was confirmed by subsequent BS-seq (H). Note that the hypermethylated sites were located in the flanking region of two important transcription factor-binding sites, STAT3 and AP1, which will significantly inhibit the transcription of GFAP. BS-seq also showed a significant increase of the methylation level at GFAP transcription start site (TSS) and 5' UTR regulatory region (I), further suggesting an inhibition of GFAP transcription through DNA methylation. (J-K) MeDIP-seq and BS-seq revealed a significant decrease of methylation at the promoter region of a neuronal gene NEFM (neurofilament-M), suggesting transcriptional activation of neuronal genes during chemical reprogramming of human astrocytes into neurons. (L-M) CHIP-qPCR revealed a significant increase of histone acetylation in the NGN2 promoter region after small molecule treatment, likely caused by HDAC inhibitor VPA. (N-O) The methylation level of H3K4 increased significantly in the NGN2 promoter region (N), whereas H3K27 methylation at the NGN2 transcription start site showed a significant decrease (O), indicating epigenetic activation of NGN2 through histone modification. Data are represented as mean±SEM.

Figure 5:
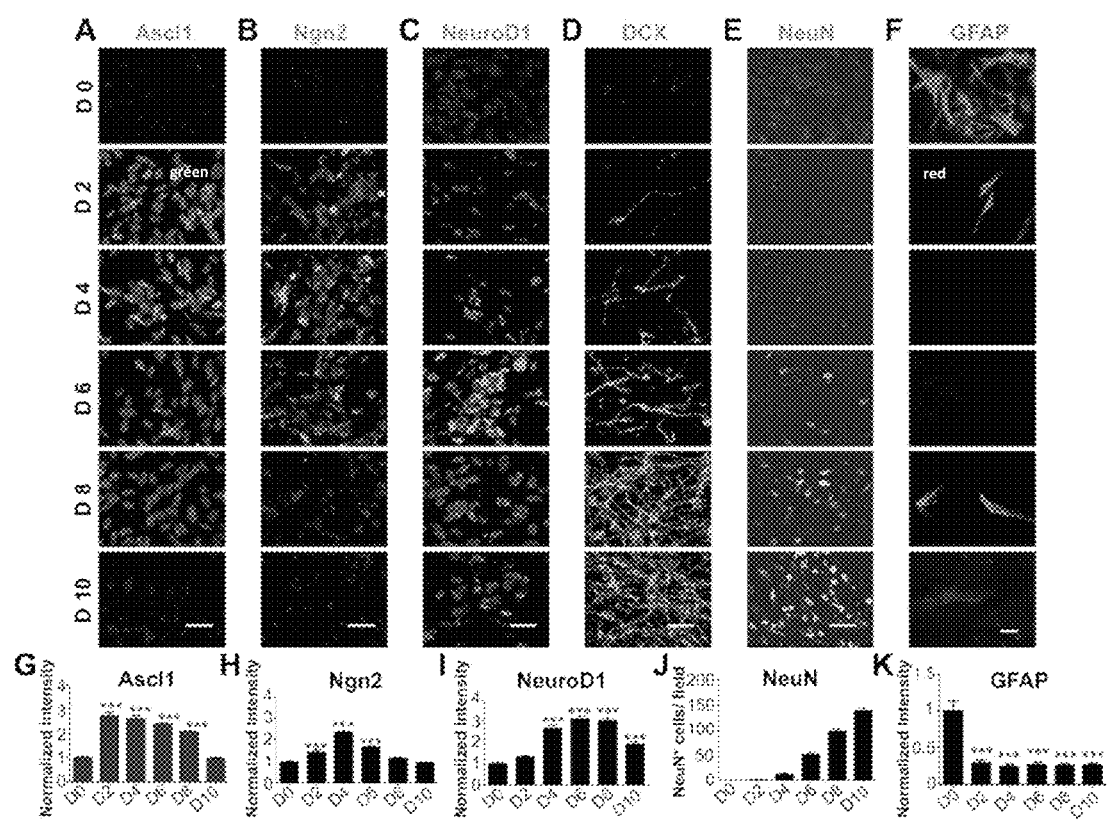

FIG. 5. Increase of the protein expression level of neural transcription factors during chemical reprogramming (A-C) Representative images illustrating the gradual activation of endogenous neural transcription factors Ascl1 (A), Ngn2 (B), and NeuroD1 (C) at different days of small molecule treatment. (D-E) Representative images showing the gradual increase of neuronal signal DCX (D) and NeuN (E) during the conversion process from D0 to D10. (F) Representative images showing the decrease of astrocytic marker GFAP from D0 to D10. Scale bars: 20 µm (G-I) Quantitative analyses of the protein expression level of Ascl1 (G), Ngn2 (H), and NeuroD1 (I). Note that Ascl1 significantly increased at day 2 by 3-fold, while Ngn2 peaked at day 4 and NeuroD1 peaked at day 6. N=3 batches. (J) Quantified data showing a significant increase of NeuN from day 6 to day 10. N=3 batches. (K) Quantified data showing a significant decrease of GFAP from D0 to D10. N=3 batches. Data are represented as mean±SEM.

Figure 6:
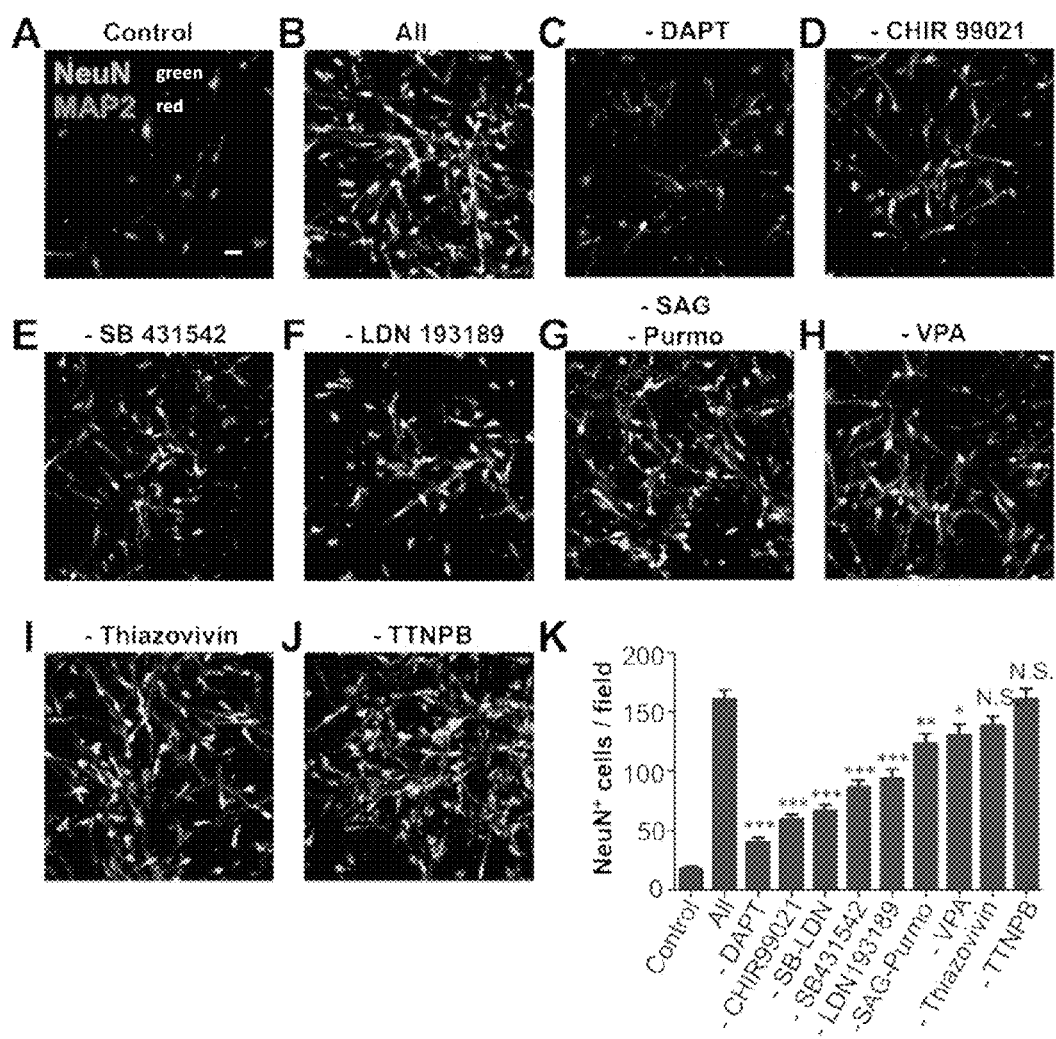

FIG. 6. Evaluating the essential role of each individual small molecule during astrocyte-neuron reprogramming (A) Human astrocytes treated with 1% DMSO as a control. NeuN, green; MAP2, red. (B) A defined combination of 9 small molecules induced a massive number of neurons (14 days post initial small molecule treatment, the same for the following removal experiments). (C-F) Individual removal of DAPT (C), CHIR99021 (D), SB431542 (E) or LDN193189 (F) from the 9 small molecule pool significantly reduced the number of converted neurons. (G) Removal of sonic hedgehog agonists SAG and Purmo together slightly reduced the number of converted neurons. (H) Removal of VPA also slightly reduced the neuronal number. (I-J) Removal of Tzv (I) or TTNPB (J) did not affect the neuronal conversion. Scale bars: 20 µm. (K) Quantitative analyses showing that DAPT is the most potent reprogramming factor, followed by CHIR99021, SB431542, and LDN193189. *$P<0.05$; $P<0.01$; *$P<0.001$; one-way ANOVA followed with Sidak's multiple comparison test. N=3 batches. Data are represented as mean±SEM.

Figure 7:
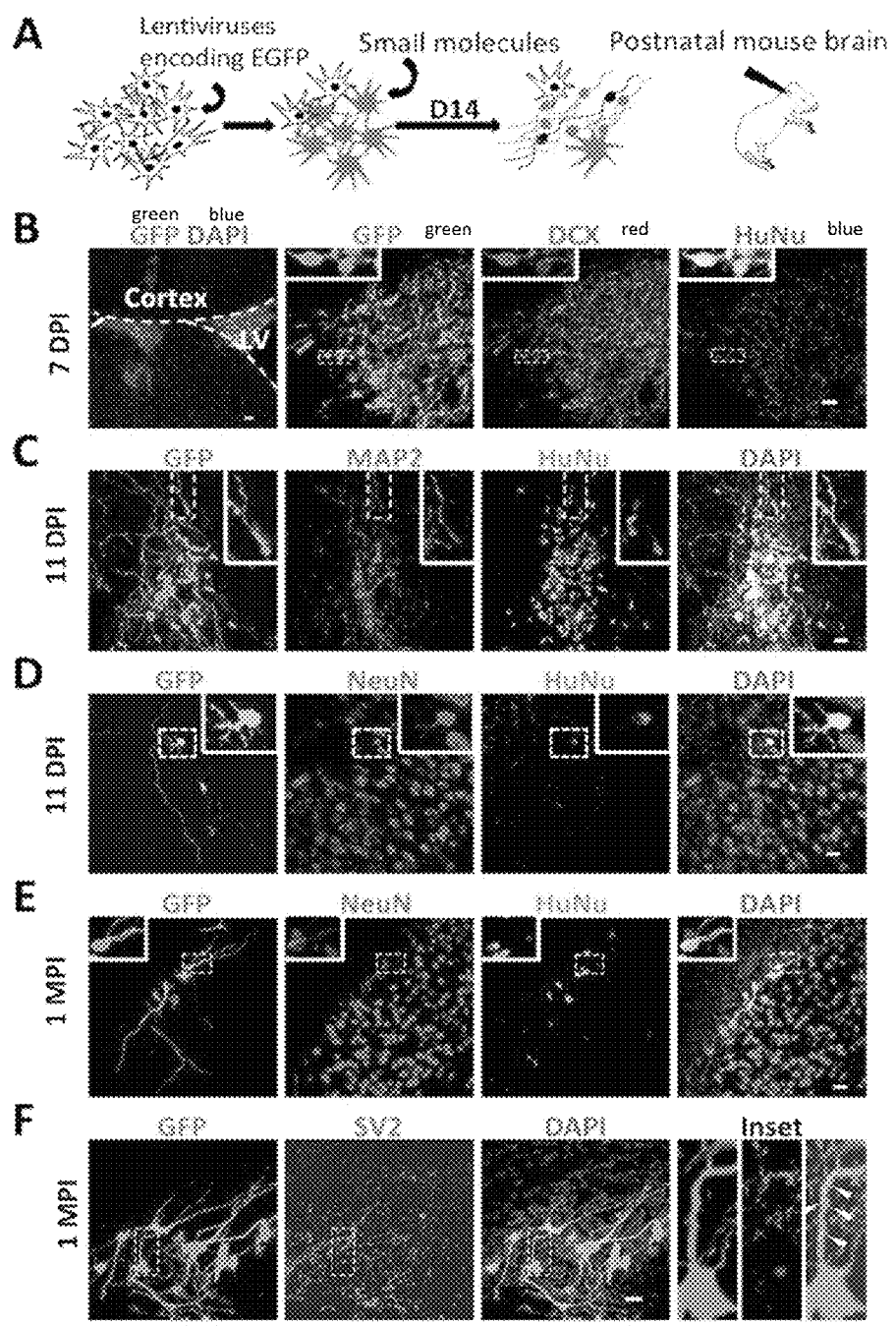

FIG. 7. In vivo survival and integration of small molecule-converted human neurons in the mouse brain. (A) Schematic drawing showing the transplantation of small molecule-converted human neurons into the mouse brains at postnatal day 1. (B) GFP-positive cells were identified around lateral ventricles at 7 days post cell injection (7 DPI). Many GFP-positive cells were also positive for DCX (red), and all of the GFP-positive cells were immunopositive for human nuclei (HuNu, Blue), indicating their human cell identity. N=6 mice. (C) At 11 DPI, some GFP-positive cells were immunopositive for MAP2 (red), indicating the survival and growth of human neurons in the mouse brain in vivo. N=6 mice. (D) Some GFP-positive human neurons, which were immunopositive for NeuN (red) and HuNu (cyan), migrated into the adjacent striatum areas and extended long neurites at 11 DPI. (E) Human neurons, labeled by NeuN (red) and HuNu (blue), survived for more than 1 month inside the mouse brain and were surrounded by mouse neurons (NeuN positive but HuNu negative). N=2 mice. (F) GFP-positive human neurons were innervated by surrounding neurons as indicated by many synaptic puncta (SV2, red) along the GFP-positive neurites (inset), suggesting the synaptic integration of the transplanted human neurons into the local neural circuit. N=2 mice. Scale bars: 20 µm.

Figure 8:
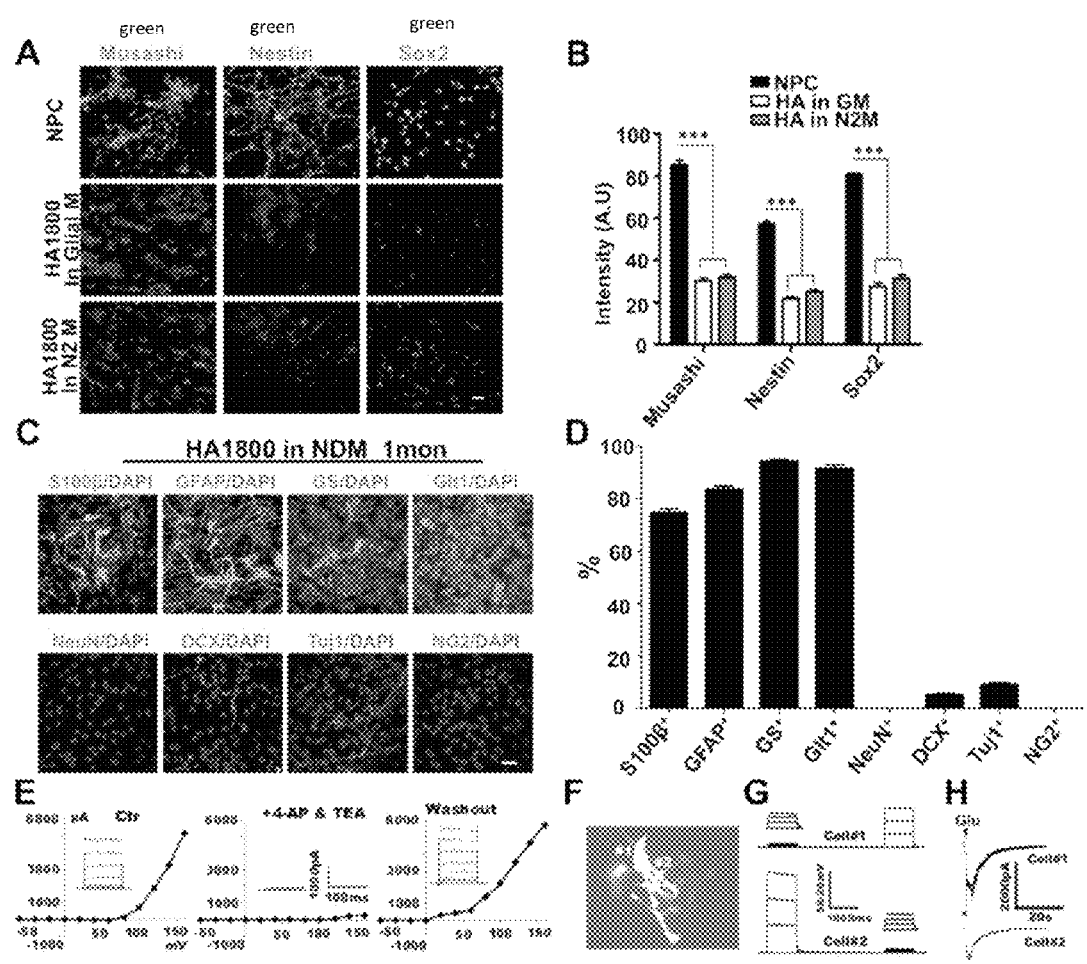

FIG. 8. Characterization of cultured human cortical astrocytes. (A) Human cortical astrocytes (HA1800, Science11) cultured in glial medium (GM, with 10% FBS) or N2 medium (for reprogramming, without FBS) and immunostained with Musashi, Nestin and Sox2. Note that in both culture media, there were no neuroprogenitor cells. (B) Quantitative analyses on neural stem cell markers revealed low expression level of Musashi, Nestin and Sox2 in cultured human astrocytes compared to human neuroprogenitors (NPCs). ***$P<0.0001$, One way ANOVA followed by Dunnett's test. N=3 batches. (C-D) Human astrocytes (HA1800, Science11) were cultured for 1 month in neuronal differentiation medium (NDM) supplemented with BDNF, NT3 and NGF to ensure neurodifferentiation if there were any neural stem cells in the astrocyte cultures. Quantitative analyses revealed that the majority of cells were immunopositive for astrocytic marker S100β (74.7±1.5%), GFAP (83.6±1.2%), Glutamate synthetase (GS) (94.3±0.7%) and GLT-1 (91.4±1.5%). A few cells were stained positive for DCX (5.18±0.67) and Tuj1 (8.98±0.75%), but no positive cells for NeuN nor NG2. N=4 batches. Scale bars=20 µm. (E-H) Functional analyses of cultured human astrocytes (HA1800). Electrophysiological recordings revealed large K+ current but no Na+ current (E), gap junctional coupling between neighboring astrocytes (F-G), and glutamate (500 M) transporter current (H). (F) shows dye coupling among local astrocyte domain after recording. Data are represented as mean±SEM.

Figure 9:
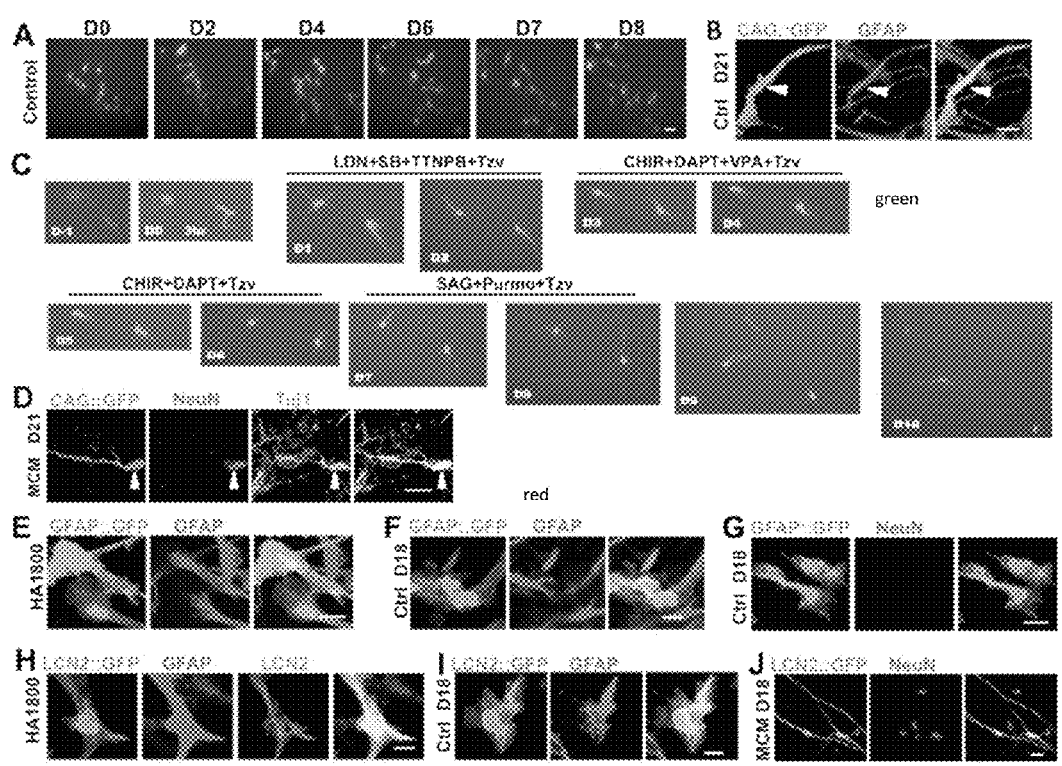

FIG. 9. Time-lapse imaging of the astrocyte-neuron conversion process during small molecule treatment (A) Human astrocytes (HAs) labeled by CAG::GFP retrovirus expressing GFP (green) remained astrocyte morphology by D8 when treated with 1% DMSO as a control. Imaged daily with a Nikon 2000 epifluorescent microscope. We used CAG::GFP retrovirus instead of GFAP::GFP retrovirus in this live cell time-lapse imaging experiment because GFAP promoter is a weak promoter, and therefore the GFP signal in GFAP::GFP-infected cells was too weak for live cell imaging. (B) Representative image showing GFP+ cells in control group were immunopositive for astrocytic marker GFAP (red) after 21 days of culture. (C) Two GFP-labeled human astrocytes were monitored from one day before to 10 days after small molecule treatment. There was a clear transition of cell morphology from astrocytes at D0 to neuron-like cells at D9. (D) After time-lapse imaging, cells were fixed at D21 and immunostained with neuronal markers NeuN and Tuj1. The GFP-labeled cells (green, arrow head) after small molecule treatment were immunopositive for NeuN (red) and Tuj1 (cyan). Scale bars=20 µm. (E-G) Human astrocytes were infected with GFAP::GFP retroviruses for lineage tracing. GFAP::GFP infected cells were all GFAP+(E, red). Without small molecule treatment, GFP+ cells were still GFAP+ astrocytes (F, red), with no neurons detected (G) after 18 days of culture. N=3 batches. Scale bars=10 µm. See FIG. 8H for small molecule-treated group. (H-J) Human astrocytes infected with LCN2::GFP retroviruses were immunopositive for GFAP (H, red) and LCN2 (H, cyan). Without small molecule treatment, GFP+ cells remained astrocyte morphology and immunopositive for GFAP (I, red) after 18 days of culture. In contrast, after small molecule treatment, GFP+ cells were immunopositive for NeuN (J, red). N=3 batches. Scale bars=10 µm.

Figure 10:
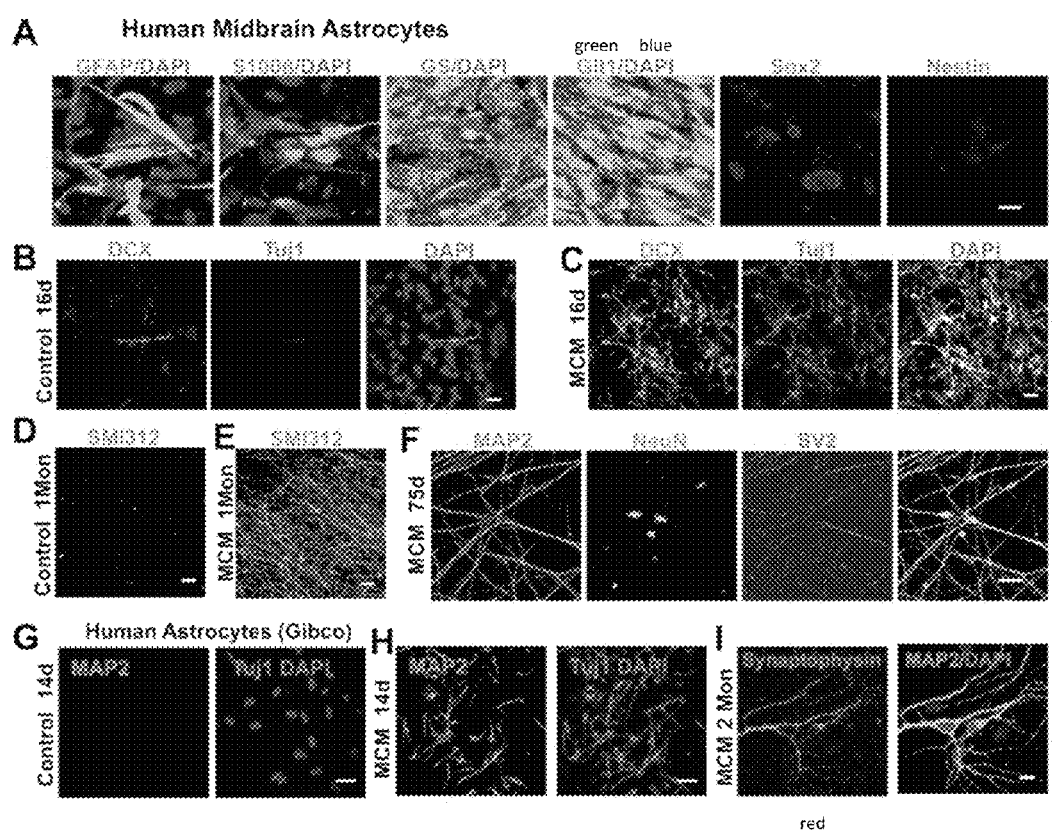

FIG. 10. Conversion of human astoryctes from different sources into neurons. (A) Characterization of human midbrain astrocytes (HA midbrain, Science11), which were immunopositive for astroglial markers GFAP, S100β, GS and Glt1, but showed Low expression level of neural stem cell markers Sox2 and Nestin. (B) Control human midbrain astrocyte cultures without small molecule treatment had very few cells immunopositive for neuronal markers DCX (green) or β-III tubulin (Tuj1, red). (C) Sequential exposure of human midbrain astrocytes to small molecules resulted into a large number of neuronal cells, which were immunopositive for DCX (green) and Tuj1 (red). Analyzed at 16 days after initial small molecule treatment. (D-E) Immunostaining images of axonal marker SMI312 (green) at 1-month old culture of human midbrain astrocytes without (D) or with small molecule treatment (E). (F) Long-term survival of human neurons converted from human midbrain astrocytes. A large number of synaptic puncta (SV2, red) were distributed along dendrites (MAP2, green) in NeuN positive (cyan) neurons. (G-H) Human brain astrocytes from a different source (Gibco) were also successfully reprogrammed into neurons using the same small molecule protocol with an efficiency of 41.1±3.6%. N=4 batches. (I) Immunostaining showing synaptophysin (red) and MAP2 (green) signal in 2-month old neurons converted from Gibco human astrocytes. Thus, different sources of human brain astrocytes could be successfully converted into neurons using the same small molecule strategy. Scale bars for panel A and I are 10 µm, and the rest are 20 µm.

Figure 11:
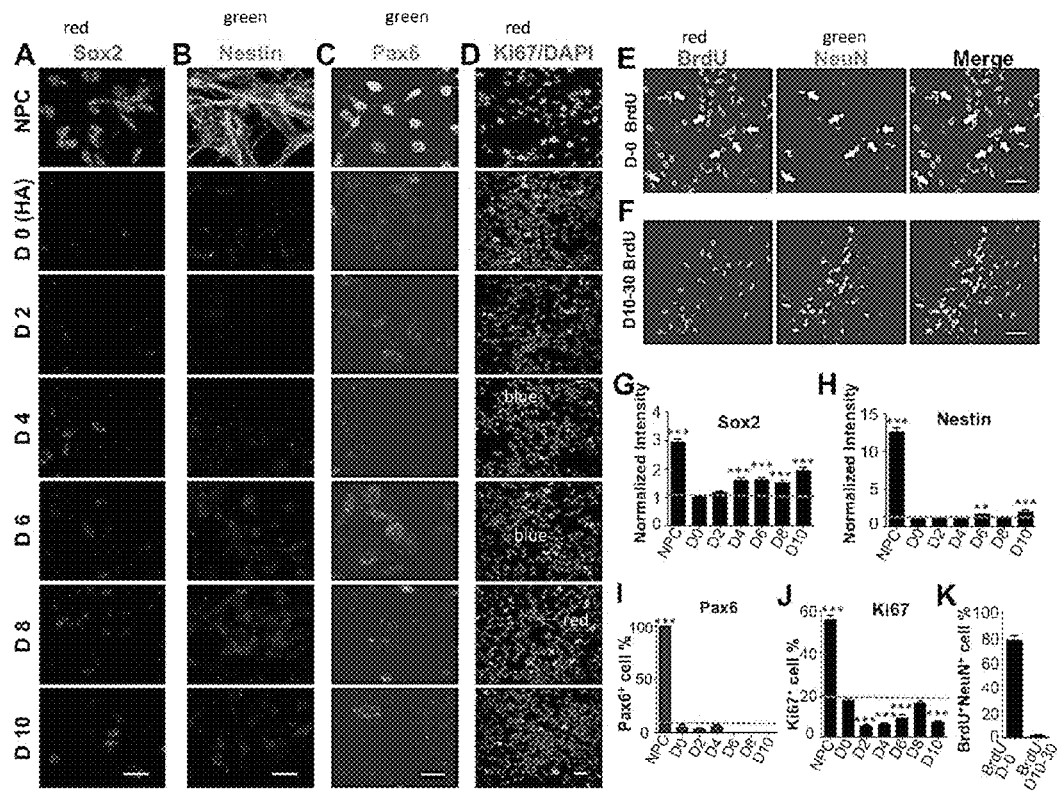

FIG. 11. Human astrocytes were directly converted into neurons without a stem cell stage. (A-C) Representative images showing low expression level of neural stem cell markers Sox2 (A, red), Nestin (B, green), and Pax6 (green) at different days of small molecule treatment compared to human NPC culture. (D) Representative images showing no significant cell expansion during reprogramming, as indicated by cell proliferation marker Ki67 (red). (E-F) BrdU birth dating of astrocyte-converted neurons before and after small molecule-mediated reprogramming BrdU was applied in culture medium at 1 day before small molecule treatment (E) or 10 days after small molecule treatment (F). Cells were fixed at day 30. Arrows in (E) point to cells with colocalization of BrdU and NeuN. (G-I) Quantitative analyses of the fluorescence intensity of Sox2 (G), Nestin (H), and Pax6 (I) during chemical reprogramming, normalized to the intensity at D0. Compared to D0, Sox2 expression level was slightly increased at D4-D10 but much lower than NPC cells (G). On the other hand, Nestin expression level was very low compared to NPC cells (H). Similarly, the Pax6+ cells were also very low when compared to NPC cells (I). (J) Quantitative analyses of Ki67+ cells to assess the cell proliferation rate during chemical reprogramming. Compared to D0, cell proliferation was significantly reduced at D2-D6 after small molecule treatment. The overall proliferation rate of human astrocytes was significantly lower than NPC cells. The reduced proliferation rate in the presence of small molecules suggested that no cell expansion occurred during chemical reprogramming (K) Quantitative analyses of BrdU-labeled neurons in E-F. A large number of cells showing colocalization of BrdU and NeuN (77.3±3.8%) when BrdU was added before small molecule treatment. Very few NeuN+ cells were colocalized with BrdU if BrdU was added after small molecule treatment (D10 to D30, 1.75±0.73%), indicating that neurons were mostly converted in the presence of small molecules. N=3 batches. Scale bars=20 µm. P<0.001; *P<0.0001; One way ANOVA followed by Dunnett's multiple comparison test. Data are represented as mean±SEM.

Figure 12:
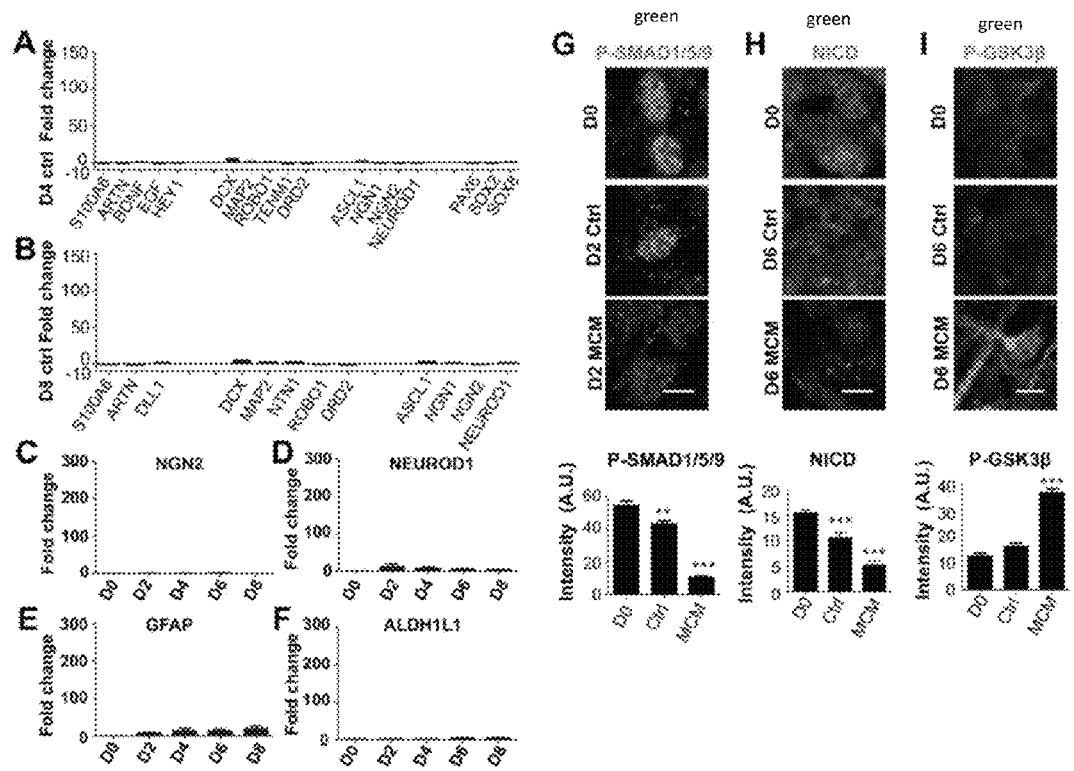

FIG. 12. Signaling pathways in small molecule-mediated reprogramming (A-B) PCR array revealed no significant gene expression change in control human astrocyte cultures at day 4 (A) or day 8 (B) without small molecule treatment, but with 1% DMSO as vehicle control. (C-F) In control human astrocyte cultures (1% DMSO), quantitative real-time PCR also revealed little transcriptional changes in neural transcriptional factors NGN2 (C) and NEUROD1 (D), or glial genes GFAP (E) and ALDH1L1 (F). N=3 batches. (G) Representative images showing the reduced level of phosphorylated SMAD1/5/9 (green) in nuclei after 2-day small molecule treatment. Quantitative analyses of the fluorescent intensity of p-SMAD1/5/9 indicating BMP signaling pathway inhibited. (H) Representative images and quantitative analysis illustrating the reduced level of Notch intracellular domain (NICD) (green) at D6 post initial small molecule treatment, indicating Notch signaling pathway inhibited. (I) Representative images and quantitative analysis illustrating the increased level of phosphorylated GSK3β (green) after 6 days treatment with small molecules, indicating that GSK3β was inactivated. P<0.001; * P<0.0001; One way ANOVA followed by Dunnett's multiple comparison test. N=3 batches. Scale bars=10 µm. Data are represented as mean±SEM.

Figure 13:
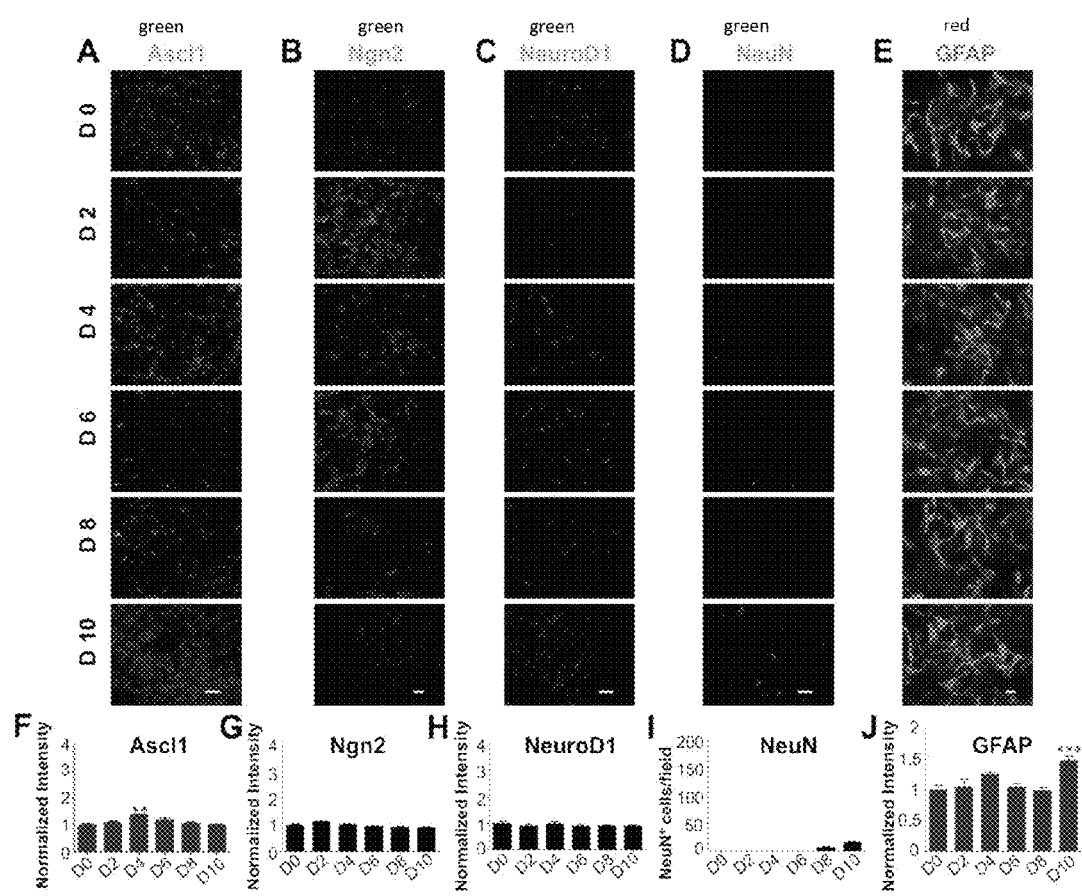

FIG. 13. No significant changes of the endogenous neural transcription factors in control human astrocytes without small molecule treatment (A-C) Immunostaining revealed very low protein expression of the endogenous neural transcription factors Ascl1 (A), Ngn2 (B) and NeuroD1 (C) in control human astrocytes (1% DMSO). (D) NeuN staining showed few neurons in control condition. (E) Representative images showing constant expression of GFAP (red) in control condition. (F-H) Quantitative analyses of the fluorescence intensity of Ascl1 (F), Ngn2 (G), and NeuroD1 (H) during D2-D10 cultures, normalized to the intensity at D0. (I) Quantitative analysis showing few NeuN-positive cells in control human astrocyte cultures from D0 to D10. (J) Quantitative analysis showing GFAP expression remained high from D0 to D10 in control human astrocyte cultures. N=3 batches. Scale bars=20 µm. Data are represented as mean±SEM.

Figure 14:
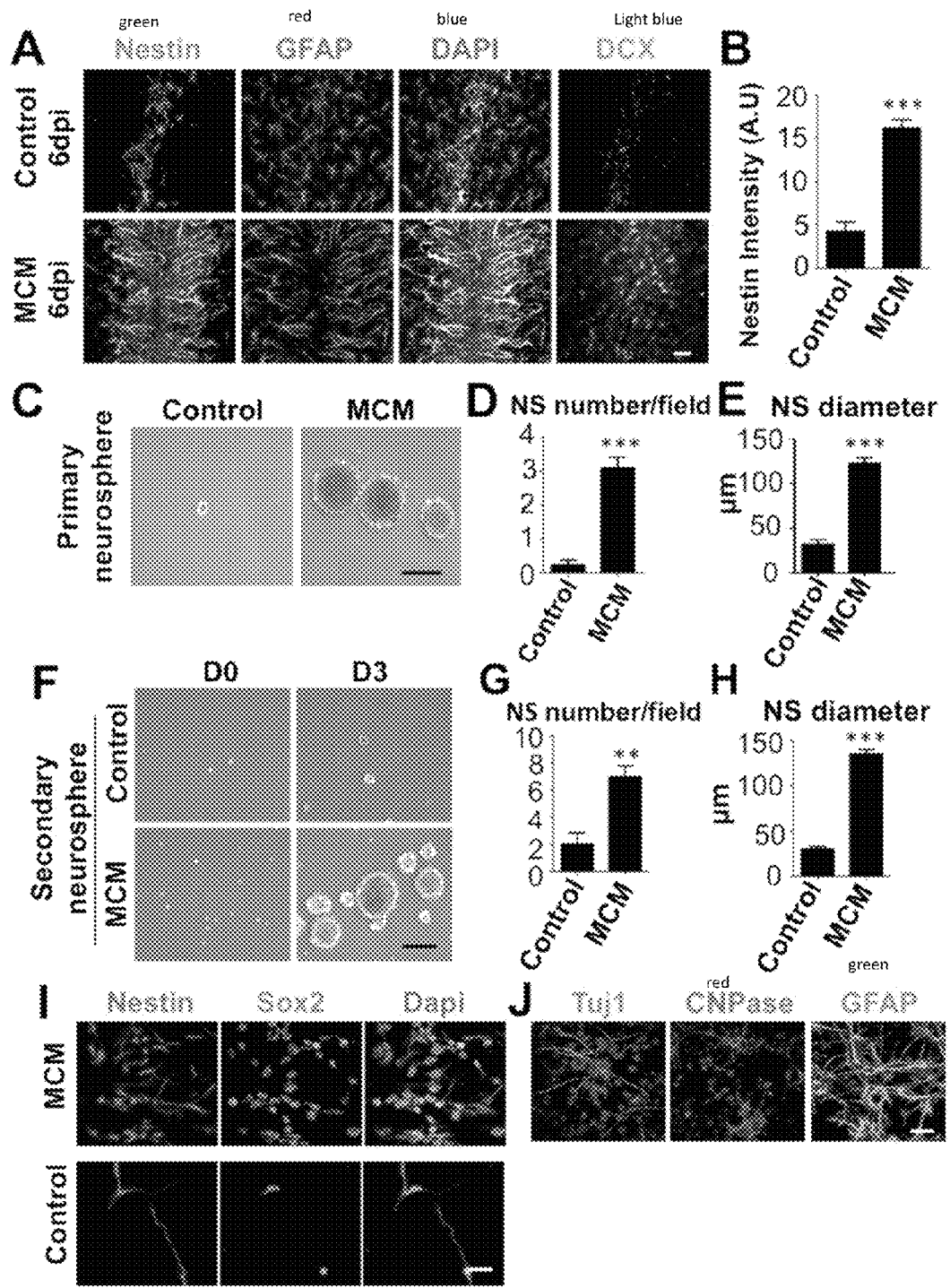

FIG. 14. Injection of small molecules in the mouse cortex in vivo promoted mouse cortical astrocytes toward neural stem cells (A) Mouse cortical astrocytes (GFAP, red) showed dramatic morphological changes and expressed high level of Nestin (green) at 6 days post single injection (dpi) of small molecules including SB431542 0.1 nmol, LDN193189 0.01 nmol, CHIR99021 0.03 nmol, DAPT 0.1 nmol, SAG 0.01 nmol and TTNPB 0.01 nmol (mixed in a total volume of 2 nl). Some DCX (cyan) expressing cells were observed around injection site. N=4 animals. (B) Quantification analyses showing increased Nestin expression in small molecule-treated mouse astrocytes in vivo (Student's t test, *P<0.0001). (C) Small molecule-treated cortical tissues were isolated and cultured in vitro. There were many more and larger primary neurospheres compared to the control cortical tissues treated with PBS containing 6% DMSO. (D-E) Quantitative analyses showing small molecule-treated cortical tissues generating more neurospheres (D) and with bigger size (E). Student's t test, *P<0.0001. (F) Primary neurospheres were subcultured and seeded as single cells. The highly proliferative single cells kept dividing to form the secondary neurospheres in suspension culture 3 days after seeding. (G-H) Quantification showing more secondary neurospheres (G) with larger size (H) formed in small molecule-treated group. Student's t test, P<0.001, *P<0.0001. (I) Cells derived from the secondary neurospheres were cultured in monolayer and immunopositive for neural stem cell markers Sox2 (green) and Nestin (red). (J) Cells derived from the secondary neurospheres were differentiated into neuronal cells (Tuj1, green) in neuronal differentiation medium, and oligodendrocytes (CNPase, red) or astrocytes (GFAP, green) in glial medium. N=3 batches. Scale bars: A, I, J=20 µm. C and F=200 µm. Data are represented as mean±SEM.

Figure 15:
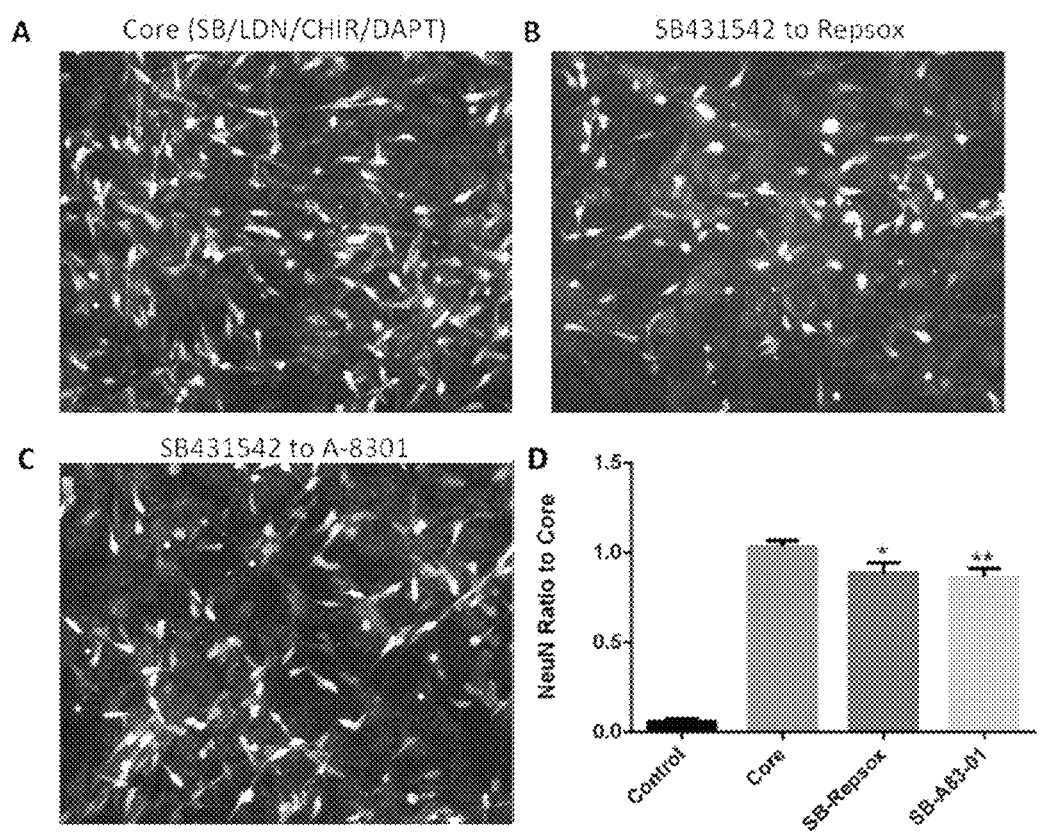

FIG. 15. Data showing A total of 4 small molecules can successfully reprogram human glial cells into neurons. (A) Core drugs, namely SB431542 5 uM, LDN193189 0.25 uM, CHIR99021 1.5 uM, DAPT 5 uM, were added to human astrocytes cell line HA1800 for six days. Medium with drugs were changed every two days. 14 days after drug addition, cells were immunostained for neuronal marker NeuN, showing many human glial cells converted into neurons. (B-C) SB431542 was replaced by its functional analogues Repsox 1 uM (B), or A-8301 0.25 uM (C). (D) Cells immunopositive for NeuN were quantified in four groups. Different batches were normalized to core groups. The conversion efficiency of SB-to-Repsox group was 88.5±5.0% of core drug group, while SB-to-A-8301 group was 86.8±5.0% of core drug group.

Figure 16:
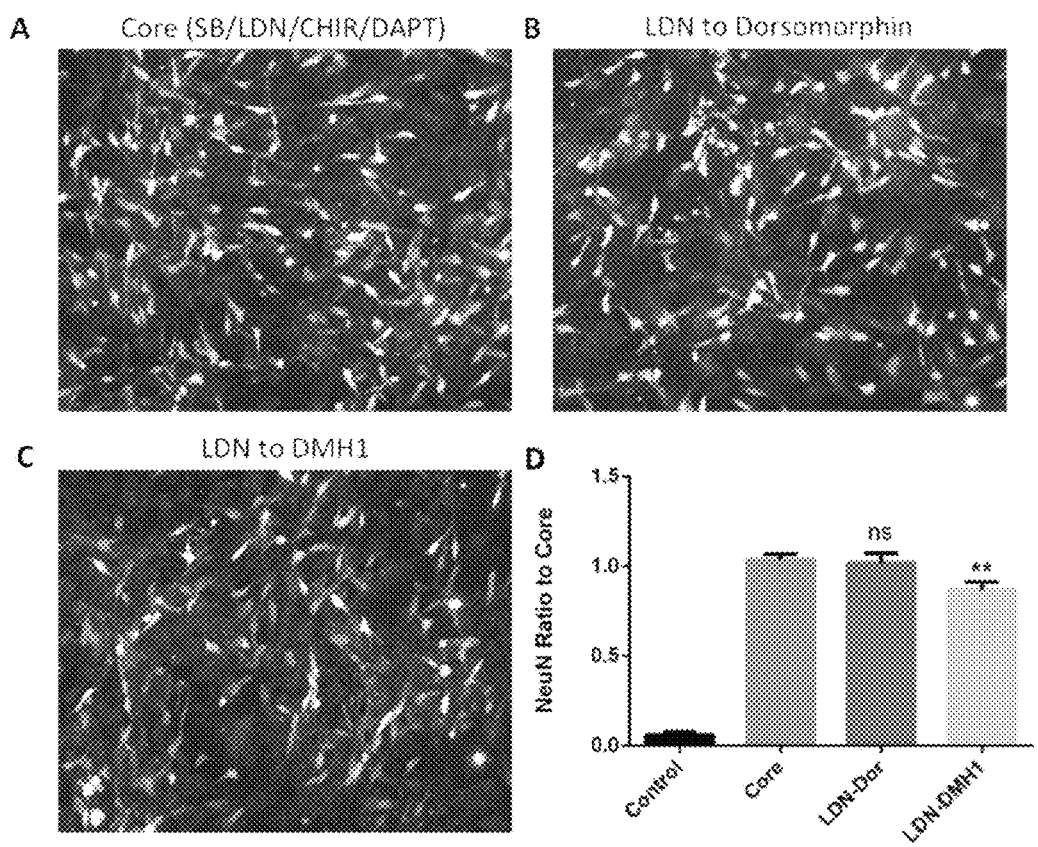

FIG. 16. Data showing efficacy of core drugs. (A) Core drugs, namely SB431542 5 uM, LDN193189 0.25 uM, CHIR99021 1.5 uM, DAPT 5 uM, were added to Human astrocytes cell line HA1800 for six days. Medium with drugs were changed every two days. 14 days after drug addition, cells were immunostained for neuronal marker NeuN. (B-C) LDN193189 was replaced by its functional analogues Dorsomorphin 1 uM (B), and DMH1 1.5 uM (C). (D) Cells immunopositive for NeuN were quantified in four groups. Different batches were normalized to core groups. LDN193189-to-Dorsomophin group achieved similar conversion efficiency to core group, while the conversion efficiency of LDN193189-to-DMH1 group was 86.8±4.9% of core group.

Figure 17:
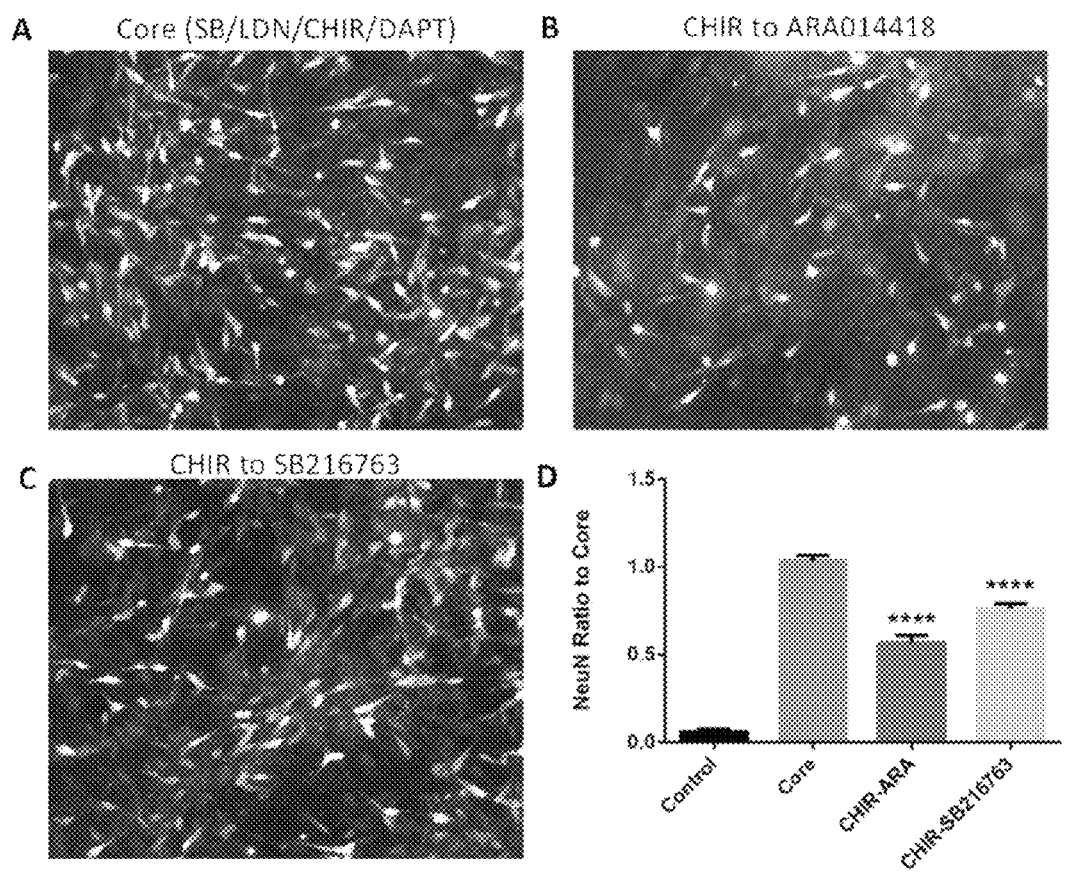

FIG. 17. Data showing efficacy of core drugs. (A) Core drugs, namely SB431542 5 uM, LDN193189 0.25 uM, CHIR99021 1.5 uM, DAPT 5 uM, were added to Human astrocytes cell line HA1800 for six days. Medium with drugs were changed every two days. 14 days after drug addition, cells were immunostained for neuronal marker NeuN. (B-C) CHIR99021 was replaced by its functional analogues ARA014418 6 uM (B), or SB216763 1 uM (C). (D) Cells immunopositive for NeuN were quantified in four groups. Different batches were normalized to core groups. The conversion efficiency of CHIR-to-ARA014418 group was 56.9±4.3 of core group, while CHIR-to-SB216763 76.07±4.2% of core group.

Figure 18:
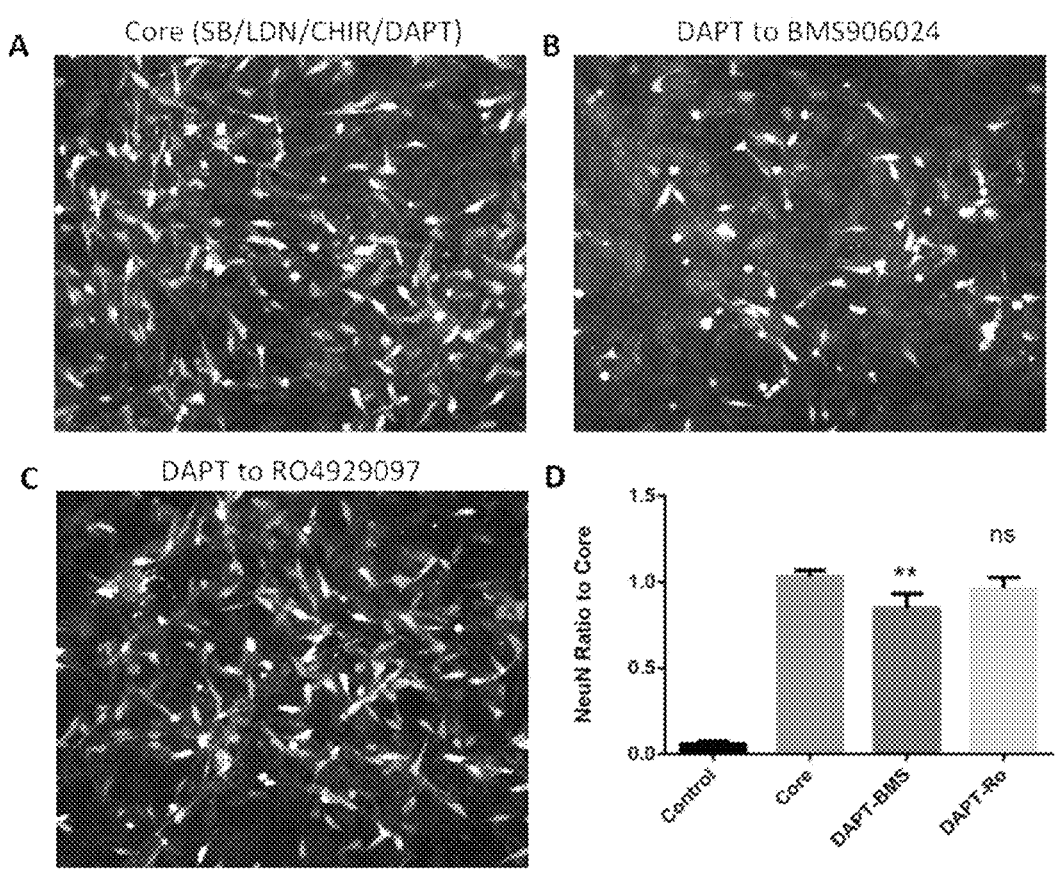

FIG. 18. Data showing efficacy of core drugs. A) Core drugs, namely SB431542 5 uM, LDN193189 0.25 uM, CHIR99021 1.5 uM, DAPT 5 uM, were added to Human astrocytes cell line HA1800 for six days. Medium with drugs were changed every two days. 14 days after drug addition, cells were immunostained for neuronal marker NeuN. (B-C) DAPT was replaced by its functional analogues BMS906024 2 uM (B), and R04929097 0.5 uM (C). (D) Cells immunopositive for NeuN were quantified in four groups. Different batches were normalized to core groups. DAPT-to-R04929097 group achieved similar conversion efficiency to core group, while the conversion efficiency of DAPT-to-BMS906024 group was 85.0±6.1% of core group.

Figure 19:
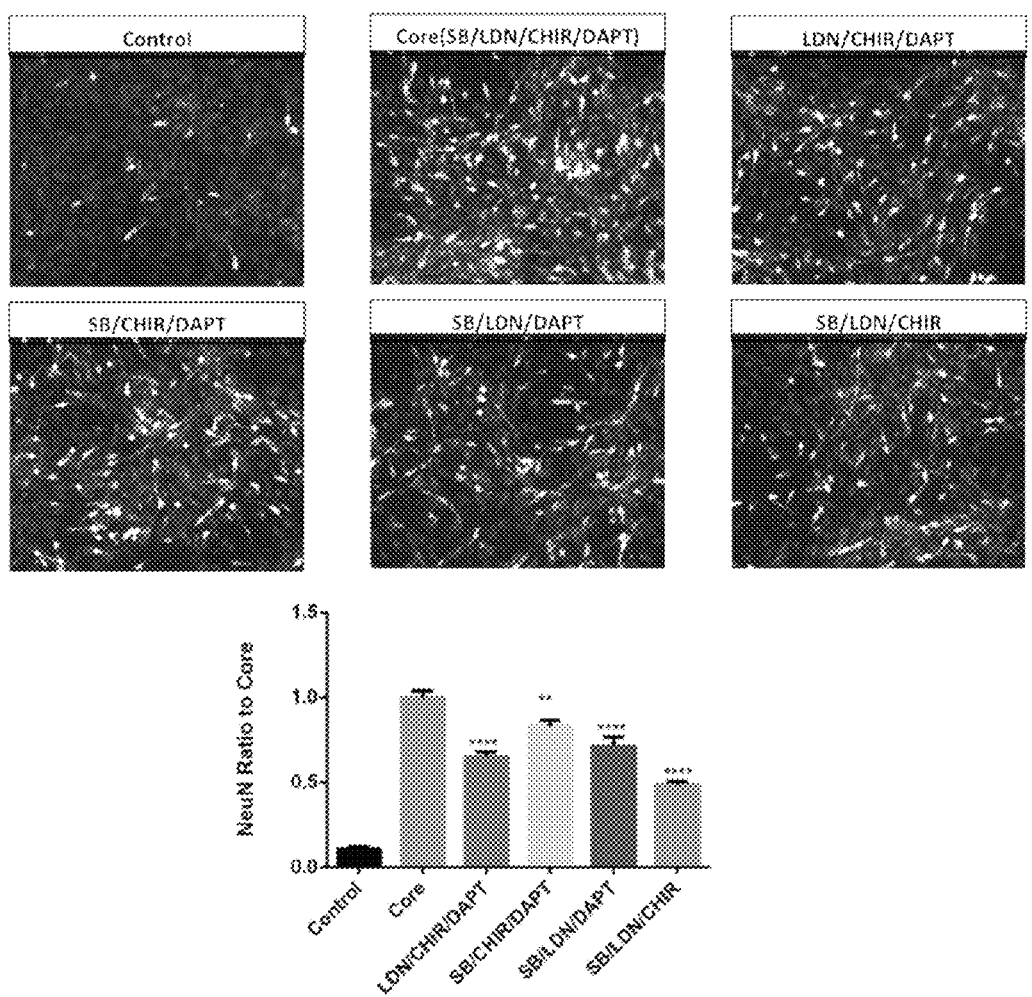

FIG. 19. Data showing any combinations of 3 drugs among SB431542, LDN193189, CHIR99021, and DAPT can reprogram human glial cells into neurons. Drugs were added for 6 days and immunostained for neuronal marker NeuN at 14 days after drug treatment. The 3-drug combination SB431542/CHIR99021/DAPT appears to be more potent than SB431542/LDN193189/CHIR99021.

DETAILED DESCRIPTION OF THE INVENTION

The present disclosure comprises compositions and methods that are designed to convert human glial cells into functional neurons. In embodiments the disclosure comprises but is not necessarily limited to reversal of glial scars to neural tissue, which is expected to be useful for a variety of therapies, non-limiting embodiments of which include brain and spinal cord repair. The method generally comprises administering to an individual in need thereof an effective amount of a combination of compounds selected from the group comprising or consisting of thiazovivin, LDN193189, SB431542, TTNPB, CHIR99021, DAPT, VPA, SAG, and purmorphamine, and combinations thereof, such that glial cells in the individual are converted into neurons. In embodiments, alternative compounds are used, where such compounds have the same or similar effect as the compounds listed above, and wherein the administration of the combination results in conversion of glial cells into neurons.

In embodiments, the disclosure is expected to be broadly applicable for therapy of any human subject in need of neuronal generation. The need for neuronal generation arises as a consequence of any of a variety of conditions, disorders or injuries that affect neuronal function, and/or reduce the number of functional neurons in the individual. Thus, the disclosure is pertinent to prophylaxis and/or therapy of conditions which include but are not necessarily limited to ischemic brain damage, such as that caused by stroke, hypoxia or other brain trauma, or glial scarring, or neurodegeneration. In embodiments the disclosure is pertinent to treating neurodegenerative disorders, including but not limited to Alzheimer's disease or other conditions which present with dementia, or Chronic Traumatic Encephalopathy (CTE) such as in athletes with a history of acute or repetitive brain trauma (i.e., concussions), or Parkinson's Disease, or Huntington's disease, or multiple sclerosis, or glioma, or spinal cord injury, or spinal muscular atrophy, or Amyotrophic lateral sclerosis (ALS).

The present disclosure is believed to be novel in view of previous approaches because it does not include introduction of modified cells or viral constructs into a subject. For example, while U.S. patent publication no. 20130183674 discloses use of cell culture media that contains the compounds SB431542, LDN1933189, SU5402, CHIR99021, and DAPT for coaxing pluripotent or multipotent stem cells to develop into nociceptor cells, it is limited to use of those compounds for in vitro differentiation of such stem cells, and importantly, this prior art process is distinct from our reprogramming of glial cells to neuronal cells, because stem cells can differentiate naturally into neurons but glial cells cannot become neurons unless subjected to a reprogramming process such as that demonstrated in this disclosure. Further, those skilled in the art will recognize that injecting cultured stem cells or their differentiated neurons into human subjects, and especially the brain poses srisk to the host. Likewise, as described above, it has been demonstrated that astroglial cells can be converted into neurons in vivo, but such approaches involve introduction of viral vectors, or other exogenous genes into the subjects which also pose particular risks to the subject.

In contrast to previous methods, the present disclosure provides in various embodiments the use of completely cell and virus free pharmaceutical formulations that comprise chemical compounds that act in concert with one another to coax glial cells to convert to neurons, and the present disclosure provides an in vivo demonstration of this process.

In embodiments, the disclosure comprises administering to a subject in need thereof an effective amount of one or more compositions comprising as an active ingredient a combination of compounds that are selected from thiazovivin, LDN193189, SB431542, TTNPB, CHIR99021, DAPT, VPA, SAG, and purmorphamine. In embodiments, distinct combinations of these compounds are administered in sequentially. Each of these compounds is known in the art and is commercially available. The disclosure includes compositions and methods that comprise any three, four, five, six, seven, eight or all nine of these compounds, and may include additional compounds as described herein or as would otherwise be apparent to one skilled in the art, given the benefit of the present disclosure. The disclosure includes pharmaceutically acceptable salts of these compounds, analogs of the compounds and salts, and compounds which exert the same or similar functions as the compounds, provided that administration of a combination of them to an individual results in conversion of glial cells to neurons.

In an embodiment, the disclosure includes administering to an individual a combination of compounds (concurrently or sequentially), wherein the combination comprises or consists of at least three of SB431542, LDN193189, CHIR 99021, and DAPT. Without intending to be bound by theory, these four compounds are from time to time referred to herein as the core compounds.

With respect to these compounds, it will be apparent to those skilled in the art that SB431542 is: -[4-(1,3-benzodioxol-5-yl)-5-(2-pyridinyl)-1H-imidazol-2-yl]benzamide and has the chemical structure:

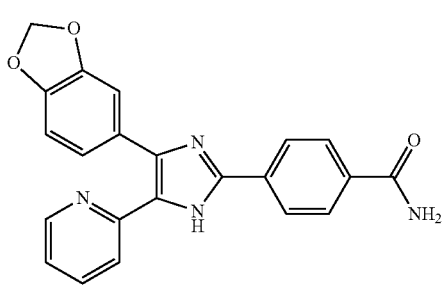 [SMILES: NC(=O)c1ccc(-c2nc(-c3ccc4c(c3)OCO4)c(-c3ccccn3)[nH]2)cc1]

LDN193189 is: 4-(6-(4-(piperazin-1-yl)phenyl)pyrazolo[1,5-a]pyrimidin-3-yl)quinoline hydrochloride and has the chemical structure:

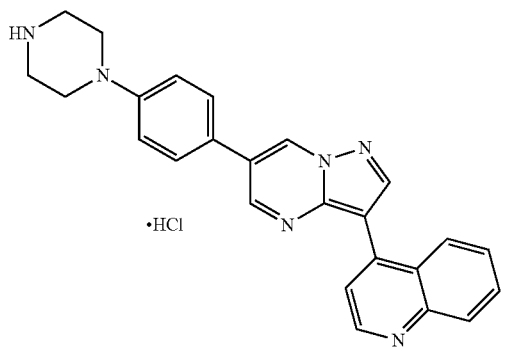 [SMILES: c1ccc2c(-c3cnn4cc(-c5ccc(N6CCNCC6)cc5)cnc34)ccnc2c1 ; Cl]

CHIR 99021 is: 6-[[2-[[4-(2,4-Dichlorophenyl)-5-(5-methyl-1H-imidazol-2-yl)-2-pyrimidinyl]amino]ethyl]amino]-3-pyridinecarbonitrile and has the chemical structure:

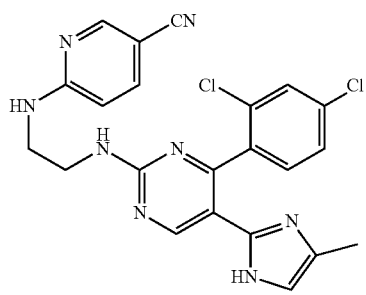 [SMILES: Cc1c[nH]c(-c2cnc(NCCNc3ccc(C#N)cn3)nc2-c2ccc(Cl)cc2Cl)n1]

DAPT is: N-[(3,5-Difluorophenyl)acetyl]-L-alanyl-2-phenyl]glycine-1,1-dimethylethyl ester and has the chemical structure:

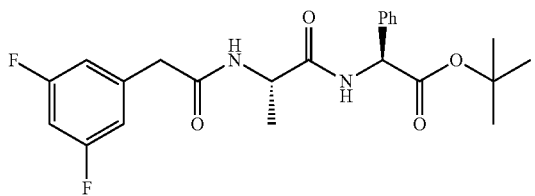 [SMILES: C[C@H](NC(=O)Cc1cc(F)cc(F)c1)C(=O)N[C@H](C(=O)OC(C)(C)C)c1ccccc1]

Those skilled in the art will recognize that, to the extent not explicitly shown in the formulae and nomenclature presented in this disclosure, each of the compounds described herein includes pharmaceutically acceptable salts thereof. It will also be recognized that SB-431542 is an inhibitor of transforming growth factor-beta superfamily type I activin receptor-like kinase (ALK) receptors ALK4, ALK5, and ALK7. LDN-193189 is an inhibitor of bone morphogenetic protein type I receptors ALK2 and ALK3. CHIR 99021 is a selective inhibitor of glycogen synthase kinase 3 (GSK-3), and DAPT is an inhibitor of gamma-secretase. Thus, other compounds having these functions (i.e., functional analogs) are included within the scope of this disclosure. In this regard, the present disclosure provides data demonstrating that use of combinations of only three drugs selected from the group of four core compounds comprising SB431542, LDN193189, CHIR99021, and DAPT can achieve glial cell to neuron reprograming. Further, the disclosure provides evidence that these four core drugs can be substituted with functional analogs and still have a similar effect, namely, to facilitate conversion of human glial cells into neurons. A "functional analog" as used herein means a compound that has a similar physical, chemical, biochemical, or pharmacological property as compared to another compound. Functional analogs may or may not have similar structures as compared to one another. In the present disclosure it is demonstrated that combining compounds that together act on signaling via Transforming growth factor beta (TGF-β), Bone morphogenetic protein (BMP), glycogen synthase kinase 3 (GSK-3), and γ-secretase/Notch pathways can reprogram glial cells into neurons. This is specifically illustrated using the drug combinations i) LDN193189/CHIR99021/DAPT, ii) SB431542/CHIR99021/DAPT, iii) LDN193189/DAPT/SB431542, and iv) LDN193189/CHIR99021/SB431542 (see Example 9 and FIGS. 15-19). Further, it is demonstrated that substituting these compounds with functional analogs can achieve the same result. For example, SB431542, a TGF-β receptor inhibitor, can be replaced with other TGF-β receptor inhibitors, such as Repsox and A8301. Likewise, LDN193189, a BMP receptor inhibitor, can be replaced by its functional analogues as demonstrated using Dorsomorphin and DMH1. CHIR9902, a GSK-3 inhibitor, can be replaced with functional analogs such as AR-A014418 and SB216763. Similarly, DAPT, a γ-secretase/Notch1 signaling inhibitor, can be replaced with BMS906024 or RO4929097, which is a pan-Notch inhibitor. Thus, in various embodiments the disclosure comprises reprogramming human glial cells into neurons by modulating the TGF-β, BMP, GSK-3, and γ-secretase/Notch signaling pathways. Additional functional analogs are described in Table 1. Thus, in certain embodiments, alternatives to SB431542, LDN193189, CHIR 99021, and DAPT that are encompassed by this disclosure include but are not necessarily limited to those described in this table:

TABLE 1

| | Compounds | Function |
|---|---|---|
| 1 | SB431542 | SB-431542 inhibits the TGF-β-mediated activation of SMAD proteins, expression of collagen and fibronectin, cell proliferation and cell motility. Potent and selective inhibitor of transforming growth factor-β superfamily type I activin receptor-like kinase (ALK) receptors. |
| | SB431542 functional analogs | |
| | Repsox | Selective inhibitor of the TGF-β type I receptor ALK5 ($IC_{50}$ values are 0.004 and 0.023 μM for ALK5 autophosphorylation and ALK5 binding respectively). |

TABLE 1-continued

| | Compounds | Function |
|---|---|---|
| | | Selective for ALK5 over a range of kinases, including p38 MAPK, JNK1 and GSK3 ($IC_{50} > 16$ μM). Enhances the efficiency of cellular reprogramming; replaces Sox2 by inducing Nanog expression. |
| | LY364947 | LY364947 is a potent ATP-competitive inhibitor of TGFβR-I with IC50 of 59 nM, shows 7-fold selectivity over TGFβR-II. |
| | LY2157299 | Potent and selective TGF-βR1 inhibitor |
| | SB525334 | Highly selective and ATP-competitive TGF-βR1 (ALK5) inhibitor |
| | A 83-01 | selective inhibitor of TGF-β type I receptor ALK5 kinase |
| | GW788388 | potent and selective ALK5 inhibitor |
| | A 77-01 | inhibitor of TGF-β type I receptor |
| 2 | LDN193189 | LDN193189 is a derivative of dorsomorphin that is a highly selective antagonist of BMP receptor isotypes ALK2 and ALK3 ($IC_{50}$ of: 5 and 30 Nm). The selectivity of LDN193189 for ALK2/3 is 200 fold over the TGF-B type receptors ALK4, -5 and -7 |
| | LDN193189 functional analogs | |
| | Dorsomorphin | Dorsomorphin is a selective inhibitor of Bone morphogenetic protein (BMP) signaling. It has been found to inhibit BMP signals required for embryogenesis and promoted significant neural differentiation from human pluripotent stem cell (Hpsc) lines. Dorsomorphin also acts as a potent, selective, reversible, and ATP-competitive inhibitor of AMPK (AMP-activated protein kinase); Ki = 109 Nm in the presence of 5 Mm ATP and the absence of AMP). |
| | LDN-212854 | potent and selective BMP receptor inhibitor |
| | ML347 | selective BMP receptor inhibitor |
| | DMH-1 | selective BMP receptor inhibitor |
| 3 | DAPT | DAPT is a γ-secretase inhibitor and indirectly an inhibitor of Notch, a γ-secretase substrate. Other γ-secretase substrates include LDL receptor-related protein, E-cadherin and ErbB-4. As an inhibitor of γ-secretase, DAPT may be useful in the study of β-amyloid (Aβ) formation. DAPT has been shown to inhibit Notch signaling in studies of autoimmune and lymphoproliferative diseases, such as ALPS and lupus erythematosus (SLE), as well as in cancer cell growth, angiogenesis, and differentiation of human induced pluripotent stem cells (Hipsc) |
| | DAPT functional analogs | |
| | BMS-906024 | BMS-906024 is a pan Notch inhibitor. BMS-906024 is a novel, potent Notch receptor inhibitor. Cancers have a tendency to relapse or to become resistant to treatments that once worked. A family of proteins called Notch is implicated in that resistance and in cancer progression more generally. BMS-906024 is in Phase I clinical trials, both alone and in combination with other agents. Patients with colon, lung, breast, and other cancers are receiving intravenous doses of the compound to determine its safety and optimum dose ranges. |
| | RO4929097 | RO4929097 is a small molecule gamma secretase inhibitor with an $IC_{50}$ of 4 Nm. It binds to gamma secretase and blocks the activation of Notch receptors, which may inhibit tumor cell proliferation. RO4929097 inhibits Notch processing in tumor cells as measured by the reduction of intracellular Notch expression by Western blot. RO4929097 produces a less transformed and flattened slower-growing phenotype but does not induce apoptosis or block tumor cell proliferation. |
| | YO-01027 (Dibenzazepine, DBZ) | Cell permeable γ-secretase inhibitor, blocks Notch pathway |
| | LY3039478 | LY3039478 is a potent Notch inhibitor with IC50 of 0.41 Nm. |
| | FLI-06 | FLI-06 is a novel inhibitor of Notch signaling with EC50 of 2.3 Mm. |
| | Begacestat | γ-secretase inhibitor; |
| | MK-0752 | Selective γ-secretase inhibitor, inhibits Notch signaling pathway |

TABLE 1-continued

| | Compounds | Function |
|---|---|---|
| | MRK 560 | γ-secretase inhibitor; inhibits proteolytic cleavage of amyloid precursor protein (APP) over the Notch pathway. Reduces levels of Aβ in the brain (inhibits Aβ40 and Aβ42 in SH-SY5Y neuroblastoma cells with an IC50 of 0.65 Nm); attenuates plaque deposition. Orally bioavailable. |
| | L-685,458 | Potent and selective γ-secretase inhibitor (IC50 = 17 Nm) that displays > 50-fold selectivity over a range of aspartyl, serine and cysteine proteases. Exhibits equal potency for inhibition of Aβ40 and Aβ42 peptides (IC50 values are 48 and 67 Nm respectively in human neuroblastoma cells). Also regulates CXCR4 and VEGFR2 expression through inhibition of Notch signaling in vitro |
| | LK 6 | Inhibitor of γ-secretase that selectively inhibits Bapp cleavage without affecting other γ-secretase-mediated pathways. Prevents recovery of Aβ40 and Aβ42 from HEK293 cell overexpressing wild-type or Swedish-mutated Bapp (IC50~30 Mm) but displays no effect on Notch cleavage and Notch-mediated intracellular signaling. Displays no activity on BACE1, BACE2, α-secretase, the ctiving e or GSK3β. |
| | Compound W | Inhibitor of γ-secretase |
| 4 | CHIR 99021 | Potent and highly selective inhibitor of glycogen synthase kinase 3 (GSK-3) (IC50 values are 6.7 and 10 Nm for GSK-3β and GSK-3α respectively). Exhibits >500-fold selectivity for GSK-3 over closely related kinases; also displays >800-fold selectivity against 45 additional enzymes and receptors. In combination with tranylcypromine, enables reprogramming of mouse embryonic fibroblasts, transduced by Oct4 and Klf4 only, into iPSCs. Enhances mouse and human ESC self-renewal when used in combination with PD 0325901. |
| | CHIR 99021 functional analogs | |
| | TWS119 | Glycogen synthase kinase 3 (GSK3) is a serine/threonine protein kinase that is inhibited by a number of extracellular stimuli such as insulin, growth factors, cell specification factors, and cell adhesion. Its activity regulates many cell functions including cell division, apoptosis, and inflammation. TWS119 is a 4,6 disubstituted pyrrolopyrimidine that potently inhibits GSK3β with an IC50 value of 30 Nm. 1 At 400 Nm, TWS119 induces neurogenesis in mouse embryonic stem cells making it a useful tool to regulate stem cell self-renewal and differentiation |
| | Tideglusib | Tideglusib (NP-12, NP031112) is a potent, selective and irreversible small molecule non-ATP-competitive GSK-3β inhibitor with an IC50 of 60 Nm. |
| | AZD1080 | selective, orally active, brain permeable GSK3 inhibitor |
| | TDZD-8 | TDZD-8 is an inhibitor of glycogen synthase kinase-3β (GSK-3β) with IC50 value of 1.4 Mm. |
| | CHIR-98014 | potent GSK-3α/β inhibitor |
| | SB 216763 | potent and selective GSK-3 inhibitor |
| | LY2090314 | potent GSK-3 inhibitor |
| | AR-A014418 | Cell-permeable GSK-3β inhibitor |
| | GSK-3 Inhibitor IX (BIO) | BIO (6-bromoindirubin-3'-oxime) is a specific inhibitor of GSK-3 with IC50 of 5 Nm for GSK-3α/β, shows >16-fold selectivity over CDK5, also a pan-JAK inhibitor. |
| | GSK-3 inhibitor 1 | GSK-3 inhibitor 1 is a potent GSK-3 inhibitor. |

In embodiments the administered combination includes the Shh agonist Smoothened agonist (SAG), which is an agonist of sonic hedgehog.

It will thus be apparent from the description, examples and figures of this disclosure that we have discovered that in combination small molecules as described herein are capable of directly reprogramming human astrocytes into functional neurons. In making this discovery we tested a variety of small molecules targeting signaling pathways that are considered to be important for inhibiting gliogenesis while activating neurogenesis. We found that the aforementioned group of small molecules is capable of reprogramming human astrocytes into neurons. In more detail, when human astrocytes were exposed simultaneously to a pool of nine small molecules together, they experienced severe cell death and the neuronal reprogramming efficiency was low, less than 10%. Instead, when a subset of the nine small molecules was administered in a sequential manner, the majority of human astrocytes (~70%) were reprogrammed into neuronal cells. We demonstrate that these small molecule-reprogrammed human neurons can survive for more than three months in culture and display robust synaptic activities. Injecting the human astrocyte-converted neurons into the mouse brain revealed that these human neurons can integrate into the local brain circuits. Together, these data demonstrate the feasibility of pure chemical reprogramming of human astrocytes into functional neurons, which is expected to result in a convenient approach to chemical delivery for therapy of a wide variety of brain injuries and neurodegenerative conditions. Moreover, our results are not limited to in vitro demonstrations because, as we demonstrate herein, administration of chemically reprogrammed human neurons to animals generates synaptic connections with endogenous neurons in mouse brain.

In general, methods of the disclosure comprise administering an effective amount of the compounds described herein to a subject such that the number of neurons in the individual is increased. In embodiments, glial cells, such as astrocytes in the individual are reprogrammed so that they are converted into neurons. In embodiments, the newly generated neurons comprise primarily glutamatergic neurons with a small proportion of GABAergic neurons. In embodiments, the disclosure is expected to facilitate development of new cortical forebrain neurons, or midbrain neurons, or hindbrain neurons, or spinal cord neurons, or combinations thereof by using methods described herein adapted as necessary by those skilled in the art in a manner that will be apparent given the benefit of the present disclosure. In embodiments the method of this disclosure is expected to result in an increase in endogenous neural transcription factors in cells that are converted into neurons. In embodiments, targeted cells demonstrate increased expression of Ascl1, Ngn2, NeuroD1, and combinations thereof. In embodiments, reprogrammed neurons are characterized by expression of neuronal markers that include but are not necessarily limited to Dcx and NeuN. In embodiments, cells in the brain, such as glial cells, are converted to neurons. In embodiments, the neurons are functional neurons. Functional neurons can exhibit properties which can comprise but are not necessarily limited to firing repetitive action potentials, developing a plurality of dendritic branches, and release of neurotransmitters, including but not necessarily limited to Glutamate (glutamic acid), dopamine, acetylcholine, serotonin, Norepinephrine (noradrenaline), and γ-Aminobutyric acid (GABA).

Compositions comprising the compounds of this disclosure can be provided in pharmaceutical formulations. The form of pharmaceutical preparation is not particularly limited, but generally comprises these active ingredients and at least one inactive ingredient. In certain embodiments suitable pharmaceutical compositions can be prepared by mixing any one or combination of the compounds with a pharmaceutically-acceptable carrier, diluent or excipient, and suitable such components are well known in the art. Some examples of such carriers, diluents and excipients can be found in: Remington: The Science and Practice of Pharmacy (2005) $21^{st}$ Edition, Philadelphia, Pa. Lippincott Williams & Wilkins. In embodiments, the pharmaceutical formulations are suitable for delivering the active ingredients across the blood-brain barrier, and/or to the spinal cord or other components of the central nervous system. Such compositions can comprise, for example, lipid formulations or other nano-particle based delivery systems.

In one embodiment the pharmaceutical formulation is suitable for oral administration, and thus can be provided in an aerosolized, liquid or solid dosage form. Solid dosage forms include but are not necessarily limited to tablets, capsules, caplets, and strips, for swallowing or oral dissolution, and may be provided for rapid or extended release, or to release distinct compounds in a desirable series over a period of time. Separate pharmaceutical compositions comprising two or any combination of the compounds can also be used. Thus the pharmaceutical formulations can comprise any two or any combination of SB431542, LDN193189, CHIR 99021, and DAPT, and any of the other functional analogues. Accordingly, in certain embodiments, LDN193189, SB431542, CHIR99021 and DAPT or a set of three of these compounds or their functional analogs may be necessary for the purpose of stimulating the reprogramming of neurons in a human subject. In embodiments, the core compounds may be necessary and sufficient to reprogram glial cells into neurons.

With respect to the administration of the pharmaceutical formulations, the route of administration can be any suitable route. In embodiments, the composition comprising the compound(s) is delivered orally. In other non-limiting embodiments, the composition is administered intravenously, parenterally, subcutaneously, intraperitoneally, transdermally, by intranasal instillation, by implantation, or intraarterially. In embodiments, an implantable medical device can be used, such as a pump, including but not limited to an osmotic pump. In embodiments the compositions comprising the compounds is delivered via an intracranial route.

Appropriate dosing of the compound(s) can be determined in conjunction with the knowledge of the skilled artisan, given the benefit of the present disclosure. In embodiments, the weight and age of the individual, personal history of neuronal damage or disease and risk for experiencing same neuronal damage, or the presence of glial scarring or reactive gliosis, may be taken into account when determining an effective amount of the active ingredient and dosing regimen. In embodiments the compounds are administered in an amount of about 0.01 nmol to about 100 nmol or higher a day, inclusive, and including all integers and ranges there between, depending on which delivering method being used. In embodiments, the compounds are provided in a single, multiple, or controlled release dose regimen. In embodiments, SB431542, LDN193189, CHIR 99021, and DAPT, and other small molecules according to this disclosure, are administered concurrently or sequentially.

In certain embodiments the disclosure includes nutraceutical compositions, which are designed to impart to an individual a beneficial effect that is related to improved neuronal health and/or function. In certain embodiments, the compositions of the invention can be used to improve the general well-being of an individual, or the cognitive capability of an individual, such as for improved memory or maintenance of memory. In embodiments the compositions are useful for improving any or all of short term memory, long term memory, or motor skills, including but not necessarily limited to gross and fine motor skills. Thus, use of nutritional supplements comprising the small molecules described herein are encompassed by this disclosure.

In one embodiment, the disclosure includes an article of manufacture. In certain aspects, the article of manufacture includes a closed or sealed package that contains two or a combination of the compounds described herein, such as in separate tablets, capsules or the like. The package can comprise one or more containers, such as closed or sealed vials, bottles, blister (bubble) packs, or any other suitable packaging for the sale, or distribution, or use of pharmaceutical agents. Thus, the package can contain pharmaceutical compositions which comprise all of SB431542, LDN193189, CHIR 99021, and DAPT, or only three of these compounds, or functional analogs, and/or other compounds that are described herein. Any two or all of these compounds can be included, and each can be provided separately or in combination with one or more of the others in the same or distinct dosage formulations so that they can be delivered concurrently, or sequentially. In one embodiment, LDN193189 or SB431542, or a combination thereof, is provided separately from CHIR99021 or DAPT, or a combination thereof.

In addition to the pharmaceutical compositions, the package may contain printed information. The printed information can be provided on a label, or on a paper insert, or printed on the packaging material itself. The printed information can include information that identifies the active agents in the package, the amounts and types of inactive ingredients, an indication of what condition(s) the pharmaceutical composition(s) is intended to treat, and instructions for taking the pharmaceutical composition, such as the number of doses to take over a given period of time, the order to take the compositions, and the like. Thus, in various embodiments the disclosure includes a pharmaceutical composition of the invention packaged in a packaging material and identified in print, on or in the packaging material, that the composition is for use in the treatment or prophylaxis of any disease, condition or disorder that is related to a deterioration of neurons, an insufficiency of neurons, or a defect in the function of neurons. In another embodiment, instead of a pharmaceutical composition, the disclosure includes a nutraceutical formulation(s), and the printed material provides information about use of such a formulation(s) for improving cognitive function, memory, motor function, overall well-being, or the like.

The following specific examples are provided to illustrate the invention, but are not intended to be limiting in any way. Where reference is made to color in a figure, labels are provided as representative samples of the referenced colors.

EXAMPLE 1

This Example demonstrates successful reprogramming of human astrocytes into neurons by small molecules as outlined above. These experiments were designed to develop a convenient method for reprogramming human astrocytes into neurons by small molecules through methods such as but not limited to oral drug administration that can be easily taken by patients. Thus, we investigated whether small molecules could replace neural transcription factors to reprogram glial cells into neurons. We used human cortical astrocytes (HA1800, ScienCell, San Diego, Calif., USA) in cultures for chemical reprogramming, aiming at clinical applications for human brain repair. We selected 20 small molecules as our starting candidate pool based on two major selection criteria: one ct to inhibit glial signaling pathways, and the other is to activate neuronal signaling pathways. Some molecules were included because they can modulate DNA or histone structure to increase reprogramming efficiency. The 20 small molecules selected for our initial screening are: SB431542, RepSox, LDN193189, dorsomorphin, DAPT, BMS-299897, CHIR99021, TWS119, Thiazovivin, Y27632, SAG, purmorphamine, TTNPB, RA, VPA, forskolin, BIX 01294, RG-108, ISX9, and Stattic.

Figure 1:
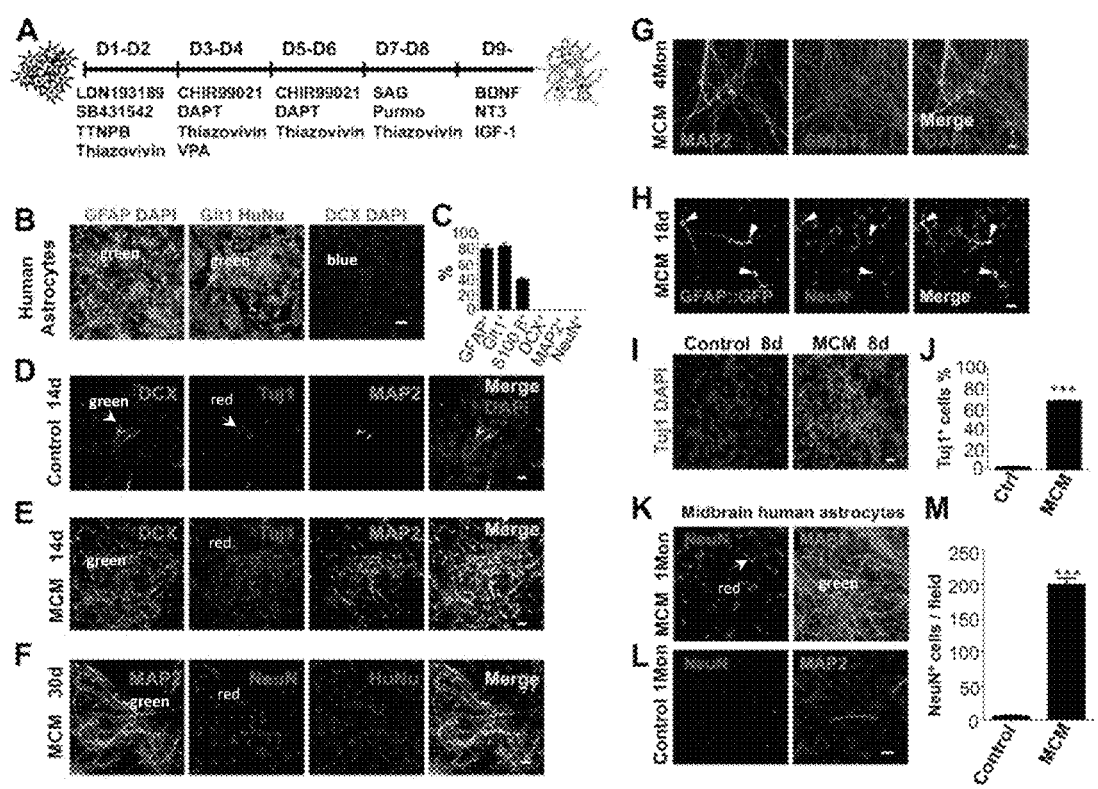
FIG. 1. Sequential exposure to a defined group of small molecules converts human astroglial cells into neuronal cells. (A) Schematic illustration of our strategy to convert cultured human astrocytes into neurons using a cocktail of small molecules. Note that different subsets of small molecules were used at different reprogramming stages. (B, C) Quantitative analysis of the human astrocyte cultures (HA1800, ScienCell). The majority of cells in our human astrocyte cultures were immunopositive for astrocytic marker GFAP (79.3±4.9%), astrocytic glutamate transporter GLT-1 (82.5±4.3%), and to a lesser degree S100β (39.3±1.8%). No cells were immunopositive for neuronal markers NeuN, MAP2 or Doublecortin (DCX). HuNu, human nuclei, marker for human cells. N=3 batches. (D) Control human astrocyte cultures without small molecule treatment had very few cells immunopositive for neuronal markers DCX (green), β-III tubulin (Tuj1, red) or MAP2 (cyan). (E) Sequential exposure of human astrocytes to small molecules resulted into a massive number of neuronal cells, which were immunopositive for DCX (green), Tuj1 (red) and MAP2 (cyan). MCM stands for master conversion molecules, including the 9 small molecules for reprogramming together. Analyzed at 14 days after initial small molecule treatment. (F) At 30 days post initial small molecule treatment, human astrocyte-converted neurons developed extensive dendrites (MAP2, green) and were immunopositive for mature neuronal marker NeuN (red). (G) Small molecule-converted human neurons survived for 4 months in culture and showed robust dendritic trees (MAP2, green) as well as extensive axons (SMI312, red). (H) Astroglial lineage tracing with GFAP::GFP retrovirus showing GFP+ cells were immunopositive for neuronal marker NeuN (red) after small molecule treatment. N=5 batches. (I and J) Small molecule treatment achieved high conversion efficiency after 8 days exposure to MCM (67.1±0.8%, Tuj1+ neurons/total cells labeled by DAPI, n=4 batches). (K) Chemical reprogramming of human midbrain astrocytes into neurons. At 1-month post initial small molecule treatment of human midbrain astrocytes (ScienCell), most cells were immunopositive for neuronal marker NeuN (red) and MAP2 (green). (L) Control human midbrain astrocyte cultures without small molecule treatment had very few cells immunopositive for NeuN (red) or MAP2 (green) at 1-month culture in neuronal differentiation medium. (M) Quantitative analysis revealed a large number of NeuN-positive neurons converted from human midbrain astrocytes at 1-month post small molecule treatment (199.7±9.2 per 40× field), whereas control group only had a few NeuN+ cells (5.6±1.4 per 40× field). N=4 batches. Scale Bars: 50 μm for panel B; 20 μm for other images. ***P<0.001, Student's t test. Data are represented as mean±SEM.

We mainly used human cortical astrocytes (HA1800, ScienCell, San Diego, Calif., USA) in primary cultures for chemical reprogramming Human astrocytes were isolated, passaged, and maintained in culture medium with 10% fetal bovine serum (FBS) to reduce possible contamination of progenitor cells, because FBS stimulates differentiation of progenitors. For initial testing, we applied a group of small molecules together to human astrocyte cultures, but massive cell death was observed after 2 days of drug treatment. To reduce cell death, we added fewer small molecules at different time points. Each molecule was tested with a series of different concentrations to find out the optimal concentration for reprogramming. After testing hundreds of different combinations we found a combination of 9 small molecules capable of reprogramming human astrocytes into neurons when added in a stepwise manner (FIG. 1A). This set of 9 small molecules is hereafter briefed as master conversion molecules (MCMs). Specifically, human astrocytes were first treated with LDN193189 (0.25 µM), SB431542 (5 µM), TTNPB (0.5 µM), and thiazovivin (Tzv, 0.5 µM) for 2 days. SB431542 is an inhibitor of TGFβ/ctiving receptors, which are involved in inhibiting neuronal fate and promoting glial fate during early neural development. Similarly, LDN193189 is an inhibitor of BMP receptors, which are members of TGFβ receptors and important for astroglial differentiation. TTNPB is an agonist of retinoic acid receptors, which have been reported to be crucial in the central nervous system patterning. We used the combination of LDN193189, SB431542, and TTNPB to initiate the reprogramming process by inhibiting glial signaling pathways and activating neuronal signaling pathways simultaneously. Tzv, an inhibitor of Rho-associated kinase (ROCK), promotes cell survival and has been reported to improve the Ipsc reprogramming efficiency. Tzv was included throughout the 8 days of reprogramming period. After initial two days of priming, we replaced the first set of 3 small molecules (LDN193189, SB431542, and TTNPB) with the second set of small molecules including CHIR99021 (1.5 µM), DAPT (5 µM), and VPA (0.5 Mm). CHIR99021 is an inhibitor of glycogen synthase kinase 3 (GSK3). GSK3 signaling promotes neural progenitor homeostasis and neocortical neural induction. DAPT (N-[N-(3,5-difluorophenacetyl)-L-alanyl]-S-phenylglycine t-butyl ester), a γ-secretase inhibitor that indirectly inhibits notch signaling pathway, efficiently induced neurodifferentiation from progenitor cells. VPA (valproic acid) is a histone deacetylase inhibitor and promotes histone acetylation. VPA was only included in the reprogramming medium for 2 days because longer exposure increased cell death, whereas CHIR99021 and DAPT were present from day 3 to day 6. In day 7 to day 8, we used SAG (0.1 µM) and purmorphamine (Purmo, 0.1 µM), two agonists for activating sonic hedgehog (Shh) signaling pathway, to complete the reprogramming process. Shh signaling is a key determinant of CNS patterning. SAG and Purmo, or Shh itself, have been used to induce neuronal differentiation from pluripotent stem cells. At day 9, we removed SAG and Purmo in the medium, and replaced with neurotrophic factors (BDNF, NT3, and IGF-1) to promote neuronal maturation after astrocyte-neuron conversion. The successful reprogramming strategy is illustrated in FIG. 1A.

Before reprogramming, we characterized the properties of human astrocytes in our cultures and found that the majority of cells were immunopositive for astrocyte markers GFAP (79.3±4.9%) and Glt1 (astrocyte-specific glutamate transporter, 82.5±4.3%) with no neurons detected (FIG. 1B-C). We found little contamination of neural stem cells in our human astrocyte cultures as shown by immunostaining with Sox2, Musashi, and Nestin (FIG. 8A-B), likely due to the presence of 10% FBS in our culture medium. This was further confirmed after culturing human astrocytes for one month in neural differentiation medium supplemented with growth factors (BDNF, NT3, and NGF): the majority of cells were immunopositive for astrocyte markers (S100β, GFAP, glutamine synthetase, Glt1) but rarely positive for neurons or NG2 cells (FIG. 8C-D). Moreover, we performed patch clamp recordings and demonstrated that our cultured human astrocytes were functional, with large $K^+$ and glutamate transporter currents but no $Na^+$ currents, and gap junctions formed among the astrocytes (FIG. 8E-H). In control reprogramming medium without small molecules (1% DMSO), very few neurons were detected in our human cortical astrocyte cultures (FIG. 1D). In contrast, after sequential exposure to small molecules, we found a large number of neuron-like cells immunopositive for neuronal markers such as Doublecortin (DCX), 133-tubulin (Tuj1), MAP2, and NeuN (FIG. 1E-F). The human astrocyte-converted neurons survived 4-5 months in our cultures, and developed robust axons and dendrites (FIG. 1G). To visualize the conversion process from astrocytes to neurons, we infected human astrocytes with 1 µl retroviruses encoding EGFP so that only a small number of EGFP-positive astrocytes were observed in each coverslip (FIG. 9). We performed time-lapse imaging to monitor the morphological changes of human astrocytes. In the absence of small molecules, human astrocytes did not change in morphology from day 0 to day 8 (FIG. 9A) and were immunopositive for glial marker GFAP (FIG. 9B). In contrast, during small molecule treatment, there was a clear transition from astroglial morphology to neuronal morphology with the extension of long neurites from day 8 to day 10 (FIG. 9C). After time-lapse imaging, we fixed the cells and performed immunostaining at day 21. The GFP-labeled neuron-like cells were indeed immunopositive for NeuN and Tuj1 (FIG. 9D). We further used GFAP::GFP retrovirus to label the astrocytes (91±6.7% of GFAP::GFP-infected cells were GFAP$^+$) and trace the astrocyte-neuron conversion process (FIG. 9E). At 18 days after small molecule treatment, GFP-labeled astrocytes were efficiently converted into NeuN$^+$ neurons (68.7±4.2%, FIG. 1H, n=5 batches); whereas control group without small molecule treatment had no neurons detected (FIG. 9F-G). Similar results were obtained using LCN2::GFP retrovirus (88.5±3% of LCN2::GFP-labeled cells were GFAP$^+$) to trace astrocyte-neuron conversion (FIG. 9H-J), with 54.4±5.3% of LCN2::GFP-labeled astrocytes became NeuN$^+$ neurons at 18 days after small molecule treatment (n=3 batches). The conversion efficiency obtained through lineage tracing experiment was similar to the overall conversion efficiency induced by small molecule treatment (FIG. 1I-J; control, 3.3±0.5% Tuj1$^+$, n=4 batches; MCM, 67.1±0.8% Tuj1$^+$, n=4 batches; p<0.0001, Student's t test).

To investigate whether human astrocytes from different origins can be reprogrammed into neurons using the same small molecule protocol, we further tested human midbrain astrocytes and human spinal cord astrocytes from ScienCell. Interestingly, human midbrain astrocytes were efficiently reprogrammed into neurons using our stepwise 9-small molecule strategy (FIG. 1K-M, FIG. 10A-F), whereas human spinal cord astrocytes could not be reprogrammed into neurons using the same protocol (data not shown). This result suggests that our chemical reprogramming protocol is more suitable for astrocytes with human brain origin. To further test whether our small molecule reprogramming strategy is generally applicable to human astrocytes from different sources, we purchased human astrocytes from Gibco and found that they could be reprogrammed into neurons as well (FIG. 10G-I). To ensure that our chemical reprogramming method does not involve the de-differentiation of human astrocytes into neuroprogenitor cells, we monitored Sox2, Nestin, Pax6 and Ki67 signals during the chemical reprogramming process from day 0 to day 10, and compared to neuroprogenitor cells (FIG. 11). While Sox2 showed some increase during reprogramming, it never reached the level of neuroprogenitor cells (FIG. 11A, G). Nestin and Pax6 did not show much increase during small molecule treatment (FIG. 11B-C, H-I). Ki67-labeled proliferating cells decreased significantly after small molecule treatment (FIG. 11D, J), suggesting that there were no progenitor cells that can expand and give rise to neurons. In addition, when we labeled human astrocytes with BrdU before chemical treatment, many converted neurons were BrdU positive (FIG. 11E, K); however, when we labeled our cell culture with BrdU at day 10 after small molecule treatment, essentially all converted neurons were negative for BrdU (FIG. 11F, K), suggesting that all glia-to-neuron conversion occurred during the presence of small molecules. Taken together, we have developed a successful strategy using a defined combination of small molecules to chemically reprogram human astrocytes into neurons.

EXAMPLE 2

Figure 2:
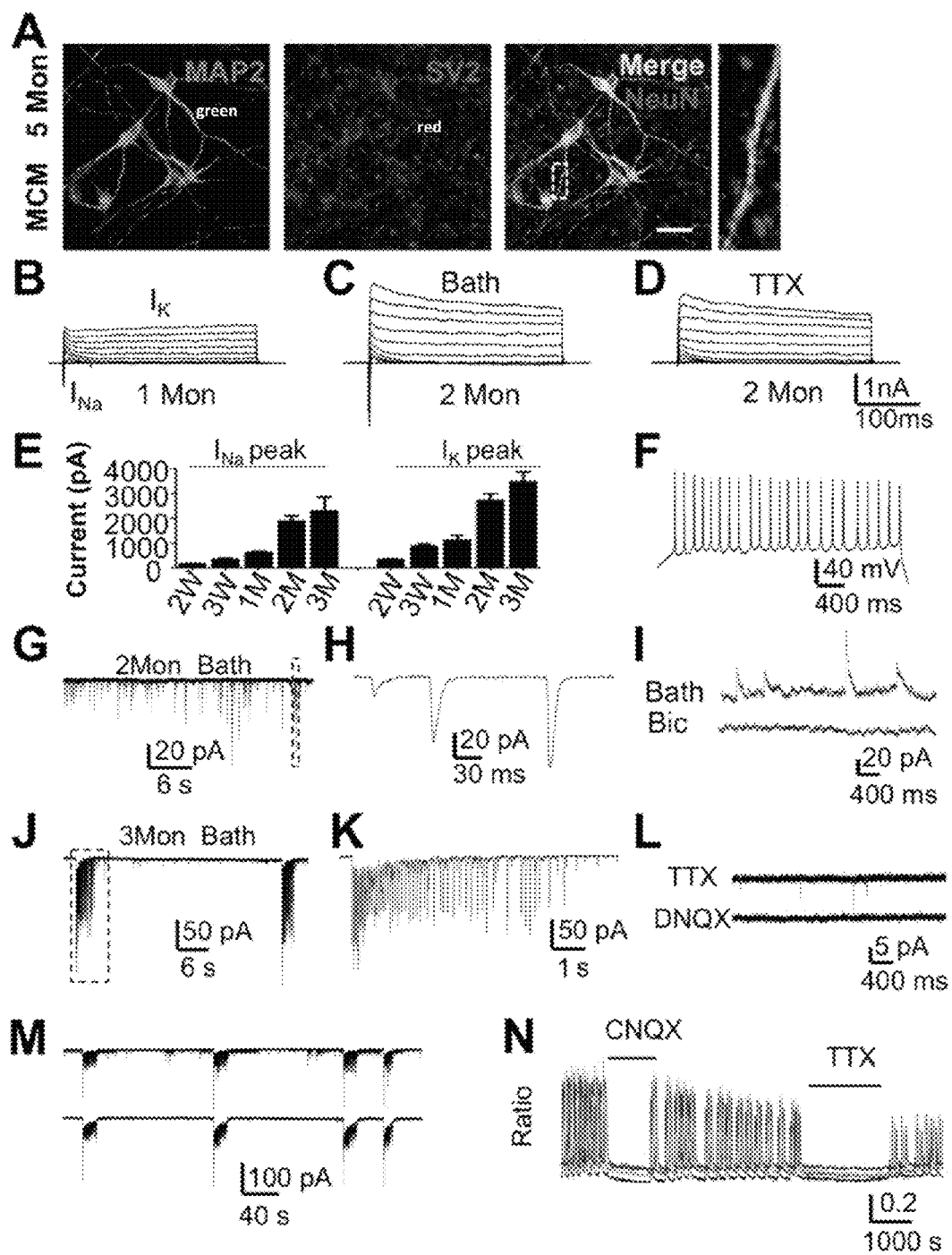
FIG. 2. Functional analyses of human astrocyte-converted neurons induced by small molecule treatment. (A) Long-term survival of small molecule-induced human neurons (5 months in culture) and massive number of synaptic puncta (SV2, red) along the dendrites (MAP2, Green). Scale bar: 20 μm. (B-D) Representative traces showing Na+ and K+ currents recorded from 1-month (B) and 2-month (C) old human neurons induced by small molecules. Panel D shows the blockade of Na+ currents by TTX (2 µM). (E) Quantitative analyses of peak Na+ and K+ currents in 2-week to 3-month old neurons converted from human astrocytes by small molecules. (F) Representative trace of repetitive action potentials recorded in small molecule-induced human neurons at 75 days post initial drug treatment. (G and H) Representative traces showing spontaneous synaptic events in 2-month old converted human neurons. Holding potential=−70 mV. (H) Expanded trace from (G). (I) Inhibitory GABAergic events revealed in human astrocyte-converted neurons when holding potential was held at 0 mV (2-month old). The events were blocked by GABAA receptor antagonist bicuculline (BIC, 10 µM). (J-K) Representative traces showing spontaneous burst activities in 3-month old small molecule-induced human neurons. HP=−70 mV. (K) Expanded view of a burst in (J). (L) The burst activities were blocked by TTX (2 µM). The majority of synaptic events at −70 mV were blocked by glutamate receptor antagonist DNQX (10 µM), suggesting that they were glutamatergic events. (M) Dual whole-cell recordings illustrating that small molecule-converted human neurons formed robust synaptic networks and fired synchronously. (N) The Ca2+ ratio imaging further illustrating that the small molecule-converted human neurons were highly connected and showed synchronous activities. Data are represented as mean±SEM.

This Example demonstrates that the small molecule-converted human neurons generated according to this disclosure are fully functional in terms of firing action potentials and releasing neurotransmitters. In particular, We found that the small molecule-converted neurons survived for a long time (>5 months) and showed robust synaptic puncta along dendrites (FIG. 2A). Similarly, neurons reprogrammed from the midbrain human astrocytes and the human astrocytes of Gibco also survived more than 2 months in culture with many synaptic puncta along dendrites (FIG. 10F, I). Patch clamp recordings revealed significant sodium and potassium currents in astrocyte-converted neurons, which gradually increased during neuronal maturation (FIG. 2B-E; 2-month: $I_{Na}$=1889±197 Pa, n=10; $I_K$=2722±263 Pa, n=10). These neurons were capable of firing repetitive action potentials (FIG. 2F). More importantly, small molecule-converted neurons showed robust spontaneous synaptic events, including both excitatory postsynaptic currents (EPSCs; frequency=0.66±0.14 Hz; amplitude=24.8±8.2 Pa, n=15) (FIG. 2G-H), and inhibitory postsynaptic currents (IPSCs; frequency=0.48±0.21 Hz; amplitude=23.3±6.3 Pa, n=2) (FIG. 2I). It is noteworthy that 3 months after initial small molecule treatment, the human astrocyte-converted neurons showed large periodic burst activities which were abolished by TTX or DNQX (FIG. 2J-L), suggesting that these neurons formed functional networks and started to fire synchronously together. In support of this notion, we performed dual whole-cell recordings and demonstrated that two adjacent neurons showed synchronous burst activities (FIG. 2M). Furthermore, we employed Fura-2 $Ca^{2+}$ ratio imaging and recorded synchronized $Ca^{2+}$ spikes in the chemically reprogrammed neurons (FIG. 2N), indicating that these neurons have been functionally networked together. Therefore, human astrocytes can be chemically reprogrammed into fully functional neurons with defined small molecules.

EXAMPLE 3

This Example demonstrates that the small molecules described herein reprogram human astrocytes into forebrain glutamatergic neurons. To characterize the neuronal properties after small molecule-induced reprogramming, we examined neuronal markers expressed from anterior to posterior nervous system. We found that the majority of human astrocyte-converted neurons were immmunopositive for forebrain marker FoxG1 (97.1±1.1%, FIG. 3A, n=3 batches), but negative for hindbrain and spinal cord markers HoxB4 and HoxC9 (FIG. 3B-C, n=3 batches). We next performed a series of immunostaining with a variety of cortical neuron markers. We found that the human astrocyte-converted neurons were largely immunonegative for cortical superficial layer marker Cux1 (FIG. 3D), but positive for deep layer markers Ctip2 (FIG. 3E, 71.4±3%, n=5 batches) and Otx1 (FIG. 3F). The human astrocyte-converted neurons were also immunopositive for forebrain neuronal marker Tbr1 (FIG. 3G, 86.4±3.4%, n=3 batches), as well as hippocampal neuronal marker Prox1 (FIG. 3H). FIG. 3I shows the quantitative results. Therefore, our chemically reprogrammed neurons are mainly forebrain deep layer neurons or hippocampal neurons.

We further investigated neuronal subtypes based on neurotransmitters they contain. We found that the majority of small molecule-reprogrammed neurons were immunopositive for glutamatergic neuron marker VgluT1 (FIG. 3J). A small fraction of the converted neurons were immunopositive for GABAergic neuron marker GAD67 (FIG. 3K). On the other hand, the astrocyte-converted neurons were largely immunonegative for cholinergic marker VAChT (FIG. 3L), dopaminergic marker TH (FIG. 3M), or spinal motor neuron marker Isl1 (FIG. 3N). The quantitative analyses of the neuronal subtypes were shown in FIG. 3O (Vglut1, 88.3±4%, n=4 batches; GAD67, 8.2±1.5%, n=4 batches). These results suggest that the glutamatergic neurons are the major subtype using our small molecule reprogramming protocol. Different small molecules may be required to reprogram human astrocytes into other neuronal subtypes.

EXAMPLE 4

This Example demonstrates the activation of endogenous neural transcription factors during chemical reprogramming. To understand the molecular mechanisms of chemical reprogramming, we first employed PCR Array (Qiagen) to investigate gene profile changes. At day 4 after small molecule treatment, we found a dramatic increase, up to 300-fold, in the transcriptional levels of several neural transcription factors including NGN1/2, NEUROD1, and ASCL1, as well as immature neuronal marker DCX (FIG. 4A). At day 8, the most significant change at the transcriptional level was the immature neuronal gene DCX, which showed 2000-fold increase (FIG. 4B), suggesting that the majority of newly converted cells are immature neurons by the end of small molecule treatment. In contrast, the glia-related genes were generally downregulated (FIG. 4A-B). We then performed quantitative real-time PCR experiments to examine the time course of transcriptional changes of NGN2, NEUROD1 and astroglial genes GFAP and ALDH1L1 during chemical reprogramming process (FIG. 4C-F). Interestingly, we found that NGN2 transcription peaked at day 4 (FIG. 4C) while NEUROD1 peaked at day 6 during small molecule treatment (FIG. 4D), consistent with their sequential expression during early brain development. As for glial genes, the GFAP transcriptional level was significantly reduced over 200-fold at D4 (FIG. 4E), coinciding with the activation of neural transcription factors (FIG. 4C-D). Similarly, the transcriptional level of another astrocytic gene ALDH1L1 was also downregulated (FIG. 4F). In contrast, control experiments without small molecule treatment showed little transcriptional changes (FIG. 12A-F). Therefore, our small molecule treatment activates neural transcriptional factors and in the meantime inhibits astrocytic genes.

EXAMPLE 5

This Example provides a description an investigation of whether epigenetic regulation was involved in our chemical reprogramming DNA methylation in gene promoter affects the accessibility of transcriptional factor binding and hence becomes a rate-limiting factor in reprogramming of pluripotent stem cells. We performed methylated DNA immunoprecipitation followed by sequencing (MeDIP-seq) to examine the methylation level of genes of interest before and after small molecule treatment. As expected, the promoter region of GFAP gene was initially unmethylated in human astrocytes before small molecule treatment (D0), but a clear increase of methylation was detected after 8 days of small molecule treatment (FIG. 4G). This increased methylation was further confirmed by targeted bisulfate sequencing (BS-seq) (FIG. 4H). Notably, this GFAP promoter region contains the transcription factor binding sites for STAT3 and AP1, which have been shown to play a critical role in the activation of GFAP gene. BS-seq data revealed that the flanking sites of STAT3 and AP1 binding region were hypermethylated (FIG. 4H), which could explain why GFAP transcription was significantly downregulated after small molecule treatment (FIG. 4E). Our MeDIP-seq also revealed an increase of DNA methylation at the GFAP transcription start site (TSS) after small molecule treatment, which was also confirmed by BS-seq (FIG. 4I). In contrast to glial gene GFAP, neuronal gene NEFM, a midsized neurofilament gene specific to neurons, showed a decrease of methylation signal at the promoter region after small molecule treatment (FIG. 4J-K), suggesting the activation of neuronal genes. We also investigated epigenetic regulation of transcription factor NGN2, an important gene involved in neuronal differentiation. MeDIP-seq analyses indicated that the methylation level of the NGN2 promoter region was quite low before and after small molecule treatment (data not shown), consistent with previous report (Covic et al., 2010). Alternative to DNA methylation, histone modification can also regulate gene expression. Therefore, we further investigated histone modification of NGN2 promoter region and transcription start site (FIG. 4L-O). Consistent with the application of HDAC inhibitor VPA during our chemical reprogramming process, we observed a significant increase of histone acetylation at D8 (FIG. 4M). Interestingly, the H3K4me3 level significantly increased at the promoter region (FIG. 4N), whereas H3K27me3 level significantly decreased at the transcription start site at D8 (FIG. 4O), consistent with transcriptional activation of NGN2 induced by small molecule treatment. Together, our results suggest that both transcriptional and epigenetic regulations are involved in our chemical reprogramming process.

To corroborate with our transcriptional and epigenetic analyses, we further performed immunostaining to examine the protein expression changes during chemical reprogramming process (FIG. 5). We found that the Ascl1 expression level first showed a significant increase after 2-day treatment with LDN193189, SB431542, and TTNPB (FIGS. 5A and G). The expression level of Ngn2 showed a peak at D4 after small molecule treatment (FIGS. 5B and H; in the presence of CHIR99021, DAPT, and VPA). Compared to Ascl1 and Ngn2, the expression of NeuroD1 appeared to be delayed, with a peak level reached at D6 after small molecule treatment (FIGS. 5C and I), consistent with our transcriptional studies (FIG. 4C-D). In addition, immunostaining experiments also revealed that some cells started to show neuronal marker such as DCX at D4-D6 (FIG. 5D), and NeuN+ neurons appeared at D8-D10 (FIGS. 5E and J), which is after the peak expression of NeuroD1. In contrast to the increase of neuronal markers, astrocytic protein GFAP showed a significant decrease after small molecule treatment (FIGS. 5F and K), consistent with epigenetic silencing and transcriptional downregulation of the GFAP gene. Control astrocytes cultured for 10 days without small molecule treatment did not show much change in the expression level of neural transcription factors, neuronal protein NeuN, or astrocytic protein GFAP (FIG. 13). These experiments suggest that our small molecule strategy has successfully activated endogenous neural transcription factors, which may play an important role in the reprogramming of astrocytes into neurons.

EXAMPLE 6

This Example describes analysis of functional roles of each individual compound during chemical reprogramming. To dissect out the contribution of each single molecule toward reprogramming, we performed a series of experiments by withdrawing each individual compound from our cocktail pool (FIG. 6). Compared to the sequential exposure to 9 molecules in total, removing DAPT resulted in a most significant reduction of the number of converted neurons (FIG. 6A-C). Similarly, removing CHIR99021 or SB431542 or LDN193189 also significantly reduced the reprogramming efficiency (FIG. 6D-F). Removing VPA or SAG+ Purmo slightly reduced the reprogramming efficiency (FIG. 6G-H). Interestingly, removing Tzv or TTNPB did not have a significant effect on the astrocyte-neuron reprogramming (FIG. 6I-J). FIG. 6K illustrates the summarized data of drug withdrawing experiments. While it is not a surprise that Tzv had no effect since it mainly acts as a cell survival factor, it was unexpected to find that removing TTNPB had no effect. We included TTNPB because it is an agonist of retinoic acid receptors, which were found to play an important role in neural differentiation. The lack of contribution of TTNPB suggested that retinoic acid may not be a necessary factor in reprogramming astrocytes into neurons. Thus the disclosure includes the proviso that the compositions do not include TTNPB. On the other hand, the inhibition of Notch signaling, GSK-3β, and BMP/TGFβ signaling pathways appeared to be important for reprogramming astrocytes into neurons. To ensure that these signaling pathways are indeed inhibited during our small molecule treatment, we performed a series of immunostaining against phosphorylated SMAD1/5/9, Notch intracellular domain (NICD), and phosphorylated GSK3β(FIG. 12G-I). Our results showed that the BMP/TGFβ, Notch, and GSK3β signaling pathways were significantly inhibited (FIG. 12G-I) after small molecule treatment, suggesting a close link between the inhibition of these signaling pathways and the astrocyte-to-neuron conversion.

EXAMPLE 7

This Example provides a demonstration of in vivo integration of human neurons in the mouse brain after reprogramming. We further investigated whether the human astrocyte-converted neurons can survive in the mouse brain in vivo. To distinguish the human astrocyte-converted neurons from pre-existing mouse neurons inside the brain, we used EGFP-lentiviruses to infect human astrocytes before small molecule treatment so that human astrocyte-converted neurons were mostly labeled by EGFP (FIG. 7A). At 14 days after initial small molecule treatment, we harvested the cells, which contained both converted neurons and non-converted astrocytes, and injected into the lateral ventricles in neonatal mice (FIG. 7A). At 7 days post cell injection (DPI), we found a cluster of EGFP-labeled cells inside the lateral ventricle, which were all immunopositive for human nuclei (HuNu, FIG. 7B), suggesting that these cells were originated from the injected human cells. Importantly, we found that many EGFP-labeled human cells were immunopositive for neuronal markers DCX (FIG. 7B), MAP2 (FIG. 7C), and NeuN (FIG. 7D), suggesting that the human astrocyte-converted neurons can survive in the mouse brain in vivo. Even one month after cell injection, we were still able to identify clusters of EGFP-labeled neurons in brain areas adjacent to the lateral ventricles such as thalamus and striatum (FIG. 7E), suggesting that the human astrocyte-converted neurons might have migrated out of the lateral ventricles and integrated into the local neural circuits. In supporting this notion, we found many synaptic puncta along the dendrites of EGFP+ human neurons (FIG. 7F), suggesting that these grafted human neurons have established synaptic connections with host neurons. Together, these in vivo experiments demonstrate that our small molecule-reprogrammed human neurons not only can survive in the mouse brain but also can integrate into the local neural circuits.

We also attempted to reprogram mouse astrocytes into neurons using our small molecule strategy both in vitro and in vivo. We found that the small molecule-treated mouse astrocytes in vivo expressed much more Nestin signal than the vehicle control (FIG. 14A-B). Therefore, we isolated the cortical tissue surrounding the small molecule injection areas and cultured in vitro. Interestingly, the small molecule-treated cortical tissue gave many more neurospheres than the vehicle control (FIG. 14C-H). These neurospheres could dissociate into neural stem cells and gave rise to neurons, astrocytes, and oligodendrocytes (FIG. 14I-J).

EXAMPLE 8

This Example provides a description of materials and methods used to obtain the data of this disclosure.

Human astrocyte culture. Human astrocytes were purchased from ScienCell (HA1800, California) or Gibco (N7805-100). Human astrocytes were primary cultures obtained from human fetal brain tissue. They were isolated and maintained in the presence of 10% fetal bovine serum (FBS), which will essentially cause any progenitor cells to differentiate. Human astrocytes were subcultured when they were over 90% confluent. For subculture, cells were trypsinized by TrypLE™ Select (Invitrogen), centrifuged for 5 min at 900 rpm, re-suspended, and plated in a culture medium consisting of DMEM/F12 (Gibco), 10% fetal bovine serum (Gibco), penicillin/streptomycin (Gibco), 3.5 Mm glucose (Sigma), and supplemented with B27 (Gibco), 10 ng/Ml epidermal growth factor (EGF, Invitrogen), and 10 ng/Ml fibroblast growth factor 2 (FGF2, Invitrogen). Cells were maintained at 37Oc in humidified air with 5% CO2.

Reprogramming human astrocytes into neurons. The astrocytes were cultured on poly-D-lysine (Sigma) coated coverslips (12 mm) at a density of 50,000 cells per coverslip in 24-well plates (BD Biosciences). The cells were cultured in human astrocyte medium until 90% confluence. At day 0 before reprogramming, half of the culture medium was replaced by N2 medium consisting of DMEM/F12 (Gibco), penicillin/streptomycin (Gibco) and N2 supplements (Gibco). The following day (Day 1), the culture medium was completely replaced by N2 medium supplemented with small molecules, or with 1% DMSO in control group. For most of the experiments using 9 molecules for reprogramming (MCM treatment), astrocytes were treated with TTNPB (0.5 µM, Tocris #0761), SB431542 (5 µM, Tocris #1614), LDN193189 (0.25 µM, Sigma #SML0559) and Thiazovivin (0.5 µM, Cayman #14245) for 2 days. At day 3, the culture medium was replaced with a different set of small molecules including CHIR99021 (1.5 µM, Tocris #4423), DAPT (5 µM, Sigma #D5942), VPA (0.5 Mm, Cayman #13033) and Thiazovivin (0.5 µM). At day 5, VPA was withdrawn by replacing medium containing only CHIR99021 (1.5 µM), DAPT (5 µM) and Thiazovivin (0.5 µM). At day 7, medium was replaced containing SAG (0.1 µM, Cayman #11914), purmophamine (Purmo, 0.1 µM, Cayman #10009634) and Thiazovivin (0.5 µM). At day 9, medium was completely replaced with neuronal differentiation medium (NDM) including DMEM/F12 (Gibco), 0.5% FBS (Gibco), 3.5 Mm glucose (Sigma), penicillin/streptomycin (Gibco), and N2 supplement (Gibco). 200 l neuronal differentiation medium was added into each well every week to keep the osmolarity constant. To promote synaptic maturation of converted neurons, brain-derived neurotrophic factor (BDNF, 20 ng/Ml, Invitrogen), Insulin-like growth factor 1 (IGF-1, 10 ng/ml, Invitrogen) and neurotrophin 3 (NT-3, 10 ng/ml, Invitrogen) were added in neuronal differentiation medium at day 9 and were refreshed every four days until day 30 (Song et al., 2002).

To examine whether our human astrocytes contain any neural stem cells, we cultured human astrocytes in neuronal differentiation medium supplemented with BDNF 20 ng/ml, NT3 10 ng/ml and NGF 10 ng/ml for 1 month. The growth factors were refreshed every 3-4 days.

The human neuroprogenitors (NPCs) derived from human pluripotent stem cells were gift from Dr. Fred Gage. The NPCs were cultured in poly-L-ornithine and laminin-coated coverslips with neuronal proliferation medium including DMEM/F12, penicillin/streptomycin, B27 supplement, N2 supplement and FGF2 (20 ng/ml) (Gibco).

Data and statistical analysis. Cell counting was performed by taking images at several randomly chosen fields per coverslip and analyzed by Image J software. The fluorescence intensity was analyzed by Image J software. Data were represented as mean±SEM. Student's t test was used for the comparison between two groups of data. One-way ANOVA and post hoc tests were used for statistical analyses of data from multiple groups.

Transplantation of small molecule-converted human neurons in vivo. In vivo experiments were conducted with wild type C57/BL6 mice. Mice were housed in a 12 hr light/dark cycle and supplied with enough food and water. Experimental protocols were approved by The Pennsylvania State University IACUC and in accordance with guidelines of the National Institutes of Health.

Human astrocytes cultured in T25 flask were transduced with 10 µl FUGW-GFP lentiviral suspension for high efficiency infection. One day after virus transduction, cells were dissociated with TrypLE and plated on poly-D-lysine-coated coverslips at a density of 50,000 cells per coverslip in 24-well plates. When cells reached 90% confluence, about 70% cells were GFP positive. After GFP infection, human astrocytes were treated with small molecules according to the protocol described above. At day 14 after initial small molecule treatment, the mixture of human astrocytes and converted neurons was dissociated with Accutase (Gibco) and resuspended with 20 µl neuronal differentiation medium supplemented with 10 ng/ml BDNF, 10 ng/ml NT3 and 10 ng/ml IGF-1. Cell suspension containing $2 \times 10^5$ cells were injected into the lateral ventricles of newborn mouse pups (postnatal day 1, P1), with 2 µl injected into each hemisphere. Cells were injected 1.5 mm anterior and 1.5 mm lateral from the lambda, with a depth of 1 mm using a stereotaxic device (Hamilton). Brains were collected at 7, 11, 14 days and 1 month post injection for analysis.

Immunocytochemistry. For brain section staining, the mice were anesthetized with 2.5% Avertin and then perfused with ice cold artificial cerebral spinal fluid (ACSF) including: 124 Mm NaCl, 26 Mm NaHCO$_3$, 10 Mm Glucose, 1.3 Mm MgSO$_4$, 1.25 Mm NaH2PO$_4$, 2.5 Mm KCl, 2.5 Mm CaCl$_2$. The brains were removed and post fixed in 4% paraformaldehyde (PFA) overnight at 4° C. Brains from young mice (<1 month old) were dehydrated with 30% sucrose for 2 days and cut at 50 µm sections by a cryostat (Leica). Brains for adult mice (>1 month old) were cut at 45 µm sections by a vibratome (Leica). Coronal brain sections were incubated in 2.5% normal goat serum, 2.5% normal donkey serum and 0.3% Triton X-100 in phosphate-buffered saline (PBS, Ph 7.4) for 2 hours, followed by incubation in primary antibody overnight.

For cell culture staining, the cultures were fixed in 4% PFA in PBS for 15 min at room temperature. Cells were first washed three times by PBS and then incubated in 2.5% normal goat serum, 2.5% normal donkey serum and 0.1% Triton X-100 in PBS for 30 minutes. Primary antibodies were incubated with either brain slices or cultures overnight at 4° C. in 3% normal goat serum, 2% normal donkey serum and 0.1% Triton X-100 in PBS. After additional washing in PBS, the samples were incubated with appropriate secondary antibodies conjugated to Alexa Fluor 488, Alexa 546, Alexa 647 (1:800, Molecular Probes), FITC, TRITC, or Dylight (1:500, Jackson ImmunoResearch) for 1 h at room temperature, followed by extensive washing in PBS. Coverslips were finally mounted onto a glass slide with an anti-fading mounting solution with DAPI (Invitrogen). Slides were analyzed with epifluorescent microscope (Keyence BZ-9000) or a confocal microscope (Olympus FV1000). Z-stacks of digital images were acquired and analyzed using FV10-ASW 3.0 Viewer software (Olympus).

Electrophysiology. For human astrocyte-converted neurons, whole-cell recordings were performed using Multiclamp 700A patch-clamp amplifier (Molecular Devices, Palo Alto, Calif.) using known techniques. The recording chamber was constantly perfused with a bath solution consisting of 128 Mm NaCl, 30 Mm glucose, 25 Mm HEPES, 5 Mm KCl, 2 Mm CaCl$_2$, and 1 Mm MgCl$_2$. The Ph of bath solution was adjusted to 7.3 with NaOH, and osmolarity at 315-325 mOsm/L. Patch pipettes were pulled from borosilicate glass (4-6 MΩ) and filled with a pipette solution consisting of 10 Mm KCl, 125 Mm K-Gluconate, 5 Mm Na-phosphocreatine, 10 Mm HEPES, 2 Mm EGTA, 4 Mm MgATP, and 0.5 Mm Na$_2$GTP, Ph 7.3 adjusted with KOH. The series resistance was typically 10-25 MΩ. For voltage-clamp experiments, the membrane potential was typically held at −70 Mv, except the recording of IPSCs when the holding potential was set at 0 Mv. Drugs were applied through a gravity-driven drug delivery system (VC-6, Harvard Apparatus, Hamden, Conn.). To monitor gap junctions between human astrocytes, 2 Mm sulphorhodamine B (SRB) dye (MW=559 Da) was added in the pipette solution.

Data were acquired using pClamp 9 software (Molecular Devices, Palo Alto, Calif.), sampled at 10 kHz and filtered at 1 kHz. Na$^+$ and K$^+$ currents and action potentials were analyzed using pClamp 9 Clampfit software. Spontaneous synaptic events were analyzed using MiniAnalysis software (Synaptosoft, Decatur, Ga.). All experiments were conducted at room temperature (22-24° C.).

RNA Extraction

Macherey-Nagel NucleoSpin® RNA kit was used to extract RNA from human cortical astrocytes during the chemical treatment at D0, 2, 4, 6, 8, and 10. For each well of 24-well plate, 350 µl of lysis buffer were added and cell lysates were collected. RNA purification was conducted with NucleoSpin® RNA Column and pure RNA was eluted with 40 µl Rnase-free $H_2O$, yielding RNA concentration ranging from 100 to 300 ng/µl per well. NanoDrop was used to measure RNA concentration and to check RNA quality. All isolated RNA had $A_{260}/A_{280}$ ratio between 2 and 2.1, which indicates RNA purity. Isolated RNA was stored at −80° C.

cDNA Synthesis and Quantitative Real Time PCR

For quantitative Real time PCR (Qrt-PCR), Cdna synthesis was done using Quanta Biosciences gScript™ Cdna SuperMix. For each sample, 1 µg RNA was used per 20 µl of total reaction volume. Reaction mix was incubated at 25° C. for 5 min, 42° C. for 30 min, 85° C. for 5 min, and held at 4° C. Cdna product was diluted 5-fold with Rnase/Dnase-free $H_2O$. Primer sets were designed using Applied Biosystems Primer Express software and listed in Table 2. RT-Qper was done using Quanta Biosciences PerfeCTa™ SYBR® Green SuperMix, ROX™. Real-time cycler Applied Biosystems® StepOnePlus™ was used. 5 µl Cdna corresponding to 1 µg of total RNA was used in final reaction volume of 25 µl. 40 PCR cycles of 95° C. for 15 s and 65° C. for 45 s were done for amplification. Melt curve analyses was done following the PCR cycles. Comparative Ct method was used for quantification and calculation of gene expression fold changes. GAPDH was used as internal control gene, and relative gene expression was analyzed with respect to gene expression at Day 0 for control human astrocyte group. RT-Qper data had three replicates of PCR reaction for each sample.

PCR Array $RT^2$ Profiler PCR Array (Qiagen, PAHS-404ZC-12) was conducted on human astrocytes before (D0) and after small molecule treatment (D4 and D8). QIAGEN $RT^2$ First Strand Kit (Qiagen #330401) was used to synthesize Cdna from isolated RNA using NucleoSpin® RNA kit. For each 96-well PCR array plate, 0.5 µg of total RNA was mixed with 19.5 µl reverse-transcription mix and incubated at 42° C. for 15 min followed by 95° C. for 5 min. 20 µl Cdna product was diluted with 81 µl Rnase-free $H_2O$. For each 96-well PCR array plate, 101 µl diluted Cdna was mixed with $RT^2$ SYBR Green Qper mastermix (Qiagen #330522) to reach a total volume of 2700 µl. 25 µl Qper mixture were transferred to each well of PCR array plate. Real-time cycler Applied Biosystems® StepOnePlus™ was used for PCR reaction and data collection. 40 PCR cycles of 95° C. for 15 s and 60° C. for 1 min were conducted and followed by melting curve analysis. Threshold for genes was set at the same value for all $RT^2$ Profiler PCR Array runs in the same analysis. QIAGEN $RT^2$ Profiler PCR Array Data Analysis software version 3.5 was used for quantification. Gene expression at D0 was set as control.

Virus Production

The Pcag::GFP-IRES-GFP retroviral vector was a gift from Dr. Fred Gage (Salk Institute, CA). The human GFAP promoter gene was subcloned from Hgfap promoter-Cre-MP-1 (Addgene) and replaced the CAG promoter to generate Pgfap::GFP-IRES-GFP retroviral vector (Guo et al., 2014). The mouse LCN2 promoter sequence was subcloned from mouse genome and replaced the CAG promoter to generate Plcn2::GFP-IRES-GFP retroviral vector. The FUGW-EGFP lentiviral vector was generously provided by Dr. Roger Nicoll (University of California at San Francisco, San Francisco, Calif.). Retroviral particles were packaged in gpg helperfree HEK (Human embryonic kidney) cells to generate VSV-G (vesicular stomatitis virus glycoprotein)-pseudotyped retroviruses as previously described (Guo et al., 2014; Tashiro et al., 2006). Lentiviral particles were packaged in HEK 293T cells as previously described (Naldini et al., 1996). The titers of viral particles were about $10^8$ particles/ml, determined after transduction of HEK cells.

Time-Lapse Imaging

Human astrocytes cultured in T25 flasks were transduced with 1 µl Pcag::GFP-IRES-GFP retroviral suspension. Two hours after virus transduction, cells were dissociated with TrypLE and plated on poly-D-lysine-coated coverslips at a density of 50,000 cells per coverslip in 24-well plates. At day 0, only 1 or 2 GFP-positive cell clusters could be found in each well. One GFP-positive cluster was imaged under epifluorescent microscope (Nikon TE-2000-S) at day 0, 2, 4, 6, 8 and day 10 without or with small molecule treatment, which was the same as described above. To visualize the reprogramming process induced by sequential application of 9 molecules, images were taken at each time point before changing the medium containing the next group of small molecules.

Lineage Tracing Experiment

Human astrocytes were cultured in poly-D-lysine coated coverslips and infected with 2 µl Pgfap::GFP-IRES-GFP retroviral suspension for overnight. For infection with Plcn2::GFP-IRES-GFP retroviruses, cultured human astrocytes were pretreated with 100 ng/ml lipopolysaccharide (LPS) to make them reactive and expressing LCN2. Cells infected with retroviruses were then treated with small molecules or 1% DMSO. Cells were cultured for 18 days before fixed for immunostaining.

BrdU Birth Dating Assay

At 1 day before small molecule treatment, human cortical astrocytes were incubated with 5-bromo-2-deoxyuridine (BrdU) with a final concentration of 10 µM for 12 hours. The following day, BrdU containing medium was completely removed and fresh human astrocyte medium was added in culture well. About 70-80% human astrocytes were labeled by BrdU at D0. The human astrocytes labeled by BrdU were treated with small molecules and fixed at day 30 after initial small molecule treatment. In another group, 10 µM BrdU was added in neural differentiation medium at day 10 after small molecule treatment and was refreshed every 3-4 days until day 30. At day 30, cells were fixed with 4% PFA for 15 minutes at room temperature followed by 20 minutes treatment with 2 M HCl at 37° C. for DNA denaturation. After 5 washes with PBS, cells were blocked in blocking buffer (2.5% normal donkey serum, 2.5% normal goat serum, 0.1% triton in PBS) for 1 hour at RT and incubated in primary anti-BrdU antibody (Dako, 1:500) at 4° C. overnight.

Calcium Imaging

Calcium indicator Fura-2 AM (Life Technology) was loaded into the cells by incubating the human astrocyte-converted neurons in culture medium containing Fura-2 AM (2 µg/ml) for 30 min in an incubator (37° C.). Calcium concentration within the soma was monitored using a Nikon 20× Super Fluor objective (N.A. 0.75), a Hamamatsu ORCA-ER digital camera (Hamamatsu, Iwata City, Japan), and a Sutter DG5 optic switcher (Sutter Instrument, Novato, Calif.) for fast changing excitation wavelengths. Simple PCI software from Hamamatsu was used for data acquisition and analyses.

Methylated DNA Immunoprecipitation (MeDIP) and High-Throughput Sequencing

MeDIP experiments were performed according to the manufacturer's protocol (Active Motif). The enriched methylated DNA was purified by Qiagen DNA purification kit for library preparation using the NEBNext ChIP-Seq Library Prep Reagent Set for Illumina according the manufacturer's protocol. In brief, 25 ng of input genomic DNA or experimental enriched DNA were utilized for each library construction. 150-300 bp DNA fragments were selected by AMPure XP Beads (Beckman Coulter) after the adapter ligation. An Agilent 2100 BioAnalyzer was used to quantify the amplified DNA, and Qper was applied to accurately quantify the library concentration. 20 µm diluted libraries were used for sequencing. 50-cycle single-end sequencings were performed using Illumina HISeq 2000. Image processing and sequence extraction were done using the standard Illumina Pipeline.

Targeted BS-Seq

The DNA samples were applied to EpiTect Bisulfite Kit (Qiagen) following the supplier's instruction. PCR amplicons were then purified by Ampure XP bead, and eluted in 50 ul H2O. The concentration was quantified with a Qubit High Sensitivity kit and then pooled together in equal molar for each sample. Mixed amplicons were then be subjected to library preparation and Miseq deep sequencing (100× or above) following standard procedures recommended by Illumina Image analysis and base calling were performed with the standard Illumina pipelines.

To determine the DNA methylation status at GFAP transcription start site, genomic DNA was treated with sodium bisulfate using EZ DNA Methylation-Gold Kit (Zymo Research) according to manufacture's instruction. Bisulfite converted DNA was amplified using nested PCR. Purified PCR amplicons were then ligated into TOPO-TA vector (Invitrogen). Reconstructed plasmids were purified and individual clones were sequenced. Ten clones were randomly picked from each time point. Data presented were from 2 independent experiments.

Bioinformatics Analyses

Bioinformatics analysis for MeDIP-seq were performed using known techniques. Briefly, FASTQ sequence files were aligned to HG19 reference genome using Bowtie. Peaks were identified by Model-based Analysis of ChIP-Seq (MACS) software.

For BS-seq, paired-end reads were first preprocessed to remove adaptor sequences, as well as low quality sequence on both the 3' and 5'ends using Trimmomatic 0.20. Preprocessed reads were then aligned to both C to T and G to A converted sequences at the loci of our interest using Bowtie 0.12.9 (-m 1 -l 30 -n 0 -e 90 -X 550). Only uniquely mapping reads were retained and PCR duplicates were removed using MarkDuplicates (Picard Tools 1.82). To avoid counting reference positions covered by overlapping paired-end reads, overlapping regions were clipped, keeping the region of the overlap with higher quality. The original computationally converted Cs and Gs were reverted, and for each reference cytosine position the number C reads and T reads were counted using SAMTools mpileup.

Chromatin Immunoprecipitation (ChIP)-Quantitative PCR

Chromatin immunoprecipitation (ChIP) experiments were performed using a conventional approach with a minor modification. Briefly, cultured human astrocytes before or after small molecule treatment were fixed with 1% formaldehyde for 10 min and quenched by 0.125 M glycine for 5 min. The chromatin was sonicated to a range of 300-500 base pair fragments with a Bioruptor (Diagenode Inc.). Following the ChIP procedures, the eluted DNA samples were purified using the DNA clean and concentration kit (Zymo research). Enrichment was determined by Qper and normalized to total input.

Stereotaxic Injection of Small Molecules into Mouse Brain

Brain surgeries were performed on 2 month-old wild type C57BL6 mice. The mice were anesthetized by injecting 20 Ml/kg 0.25% Avertin (a mixture of 25 mg/ml of Tribromoethylethanol and 25 µl/ml T-amyl-alcohol) into the peritoneum and then placed in a stereotaxic device. Artificial eye ointment was applied to cover and protect the eye. The animals were operated with a midline scalp incision and a drilling hole on the skulls above somatosensory cortex. Each mouse received one injection (coordinate: AP 1.25 mm, ML 1.4 mm, DV −1.5 mm) of small molecule mixture or PBS containing 6% DMSO with a 2 µl syringe and a 34 gauge needle. The injection volume and flow rate were controlled as 2 µl at 0.2 µl/min. After injection, the needle was kept for at least 5 additional minutes and then slowly withdrawn.

In Vitro Cell Suspension Culture

At 6 days post small molecule injection (dpi), the animals were sacrificed with exposure to $CO_2$. The brains were dissected out and the cortical brain tissues ~1.5 mm around the injection site were isolated and chopped into 0.1×0.1 mm pieces and treated with 0.5% trypsin (Gibco) for 30 min at 37° C., followed by centrifuge at 900 G for 8 min. The cell pellet was resuspended with neuronal proliferation medium supplemented with 20 ng/ml FGF2 and 20 ng/ml EGF and ~100 cells in 10 ml medium were seeded in 6-well plate with ultra low attachment surface (Corning #3471). The growth factors were refreshed every 2-3 days. One week after initial seeding, neurospheres were observed and counted under 10× microscope (Nikon). For subculture, one-week old primary neurospheres were collected by centrifuge at 900 G for 3 min, and incubated with accutase (Gibco) for 5 min at 37° C. Cell pellet was spun down at 900 G for 5 min and triturated into single cells and then suspended in neuronal proliferation medium. At 3 days after subculture, secondary neurospheres were observed and counted under 10× microscope. For monolayer culture, 4 day-old secondary neurospheres were trypsinized and resuspended according to the above mentioned protocol. The single cells were seeded on poly-L-ornithine/laminin-coated coverslips and cultured with neuronal proliferation medium with 20 ng/ml FGF2 and 20 ng/ml EGF. When cells reach 60-70% confluence, cells were fixed with 4% PFA or induced differentiation with neuronal differentiation medium or glial medium containing DMEM/F12, 5% FBS, 50 mg/ml NaHCO3 and penicillin/streptomycin.

The following primary antibodies were used in this study:

Polyclonal anti-green fluorescent protein (GFP, chicken, 1:1000, Abcam, AB13970), polyclonal anti-Glial Fibrillary Acidic Protein (GFAP, rabbit, 1:1000, Abcam, Z0334), polyclonal anti-Glial Fibrillary Acidic Protein (GFAP, chicken, 1:1000, Millipore, AB5541), monoclonal anti S100β(mouse, 1:800, Abcam, ab66028), polyclonal anti-vesicular glutamate transporter 1 (vGluT1, rabbit, 1:1000, Synaptic Systems), polyclonal anti-vesicular glutamate transporter (SV2, mouse, 1:2000, Developmental Studies Hybridoma Bank, Iowa City), polyclonal anti-Microtubule Associated Protein 2 (MAP2, Chicken, 1:2000, Abcam, AB5392), polyclonal anti-T-box, brain, 1 (Tbr1, 1:300, rabbit, Abcam, AB31940), polyclonal anti-Prox1 (rabbit, 1:1000, ReliaTech GmbH, 102-PA32), polyclonal anti-musashi-1 (rabbit, 1:500, Neuromics, RA14128), monoclonal anti-SRY (sex determining region Y)-box 2 (Sox-2, mouse, 1:500, Abcam, AB79351), polyclonal anti-SRY (sex determining region Y)-box 2 (Sox-2, rabbit, 1:500, Millipore, AB5603), monoclonal anti-Biii tubulin (Tuj1, mouse, 1:1000, COVANCE, MMS-435P), polyclonal anti-Doublecortin (DCX, rabbit, 1:500, Abcam, AB18723), polyclonal anti-NeuN (rabbit, 1:1000, Millipore, ABN78), monoclonal anti-NG2 (mouse, 1:200, Abcam, AB50009), monoclonal anti Pan-Axonal Neurofilament Marker (SMI 312, 1:1000, mouse, Covance, SMI-312R), polyclonal anti-Glial Glutamate Transporter GLT-1 (EAAT2) (Glt1, Guinea pig, 1:2000, Millipore, AB1783), monoclonal anti-NeuroD1 (mouse, 1:1000, Abcam, ab60704), monoclonal anti-Human Nuclei (HuNu, mouse, 1:1000, Millipore, MAB1281), monoclonal anti-synaptophysin (mouse, 1:800, Millipore, MAB368), polyclonal anti-CDP (Cux1, rabbit, 1:500, Santa Cruz, sc-13024), monoclonal anti-Ctip2 (rat, 1:600, Abcam, ab18465), anti-Otx1 (mouse, 1:200, Developmental Studies Hybridoma Bank, Iowa City, otx-5F5), anti-HoxC9 (mouse, 1:200, Developmental Studies Hybridoma Bank, Iowa City, 5B5-2), anti-HoxB4 (mouse, 1:200, Developmental Studies Hybridoma Bank, Iowa City, 112 anti Hoxb4), polyclonal anti-FoxG1 (Goat, 1:1000, Abcam ab3394) polyclonal anti-vesicular acetylcholine transporter (VAChT, Guinea pig, 1:800, Millipore, AB1588), monoclonal anti-GAD67 (mouse, 1:1000 Millipore, MAB5406), anti-Isl1 (mouse, 1:200, Developmental Studies Hybridoma Bank, Iowa City, 39.4D5) monoclonal anti tyrosine hydroxylase (TH, mouse, 1:600, Millipore, MAB318), polyclonal anti neurogenin2 (Ngn2, rabbit, 1:600, Abcam, ab26190), monoclonal anti-NeuroD1 (mouse, 1:800, Abcam, ab60704), polyclonal anti-MASH1/Acheate-scute homologl (Ascl1, Rabbit, 1:800, Abcam, ab74065), Monoclonal anti Nestin (mouse, 1:800, Neuromics, MO15056), polyclonal anti Ki67 (Rabbit, 1:800, Abcam, ab15580), monoclonal anti N200 (mouse, 1:1000, Sigma, N0142), monoclonal anti BrdU (mouse, 1:500, Dako, 074401-8), monoclonal anti Glutamine Synthetase (GS, mouse, 1:800, Millipore, MAB302), monoclonal anti phosphor-GSK-33 (Ser9)(5B3) (Rabbit, 1:100, Cell signaling, 9323), monoclonal anti phosphor-Smad1(Ser463/465)/Smad5 (Ser463/465)/Smad9 (Ser465/467) (D5B10) (Rabbit, 1:600, Cell signaling, 13820), monoclonal anti Cleaved Notch1 (Val1744) (D3B8) (Rabbit, 1:200, Cell signaling, 4147), monoclonal anti CNPase (mouse, 1:800, Abcam, ab6319), polyclonal anti-Lipocalin-2/NGAL (LCN2, Goat, 1:1000, R&D, AF1857).

Following antibodies were used for DNA pull down in CHIP assay: Polyclonal anti-acetyl-Histone H3 (Rabbit, Millipore, 06-599); polyclonal anti-trimethyl-Histone H3 (Lys27) (H3K27Me3, Rabbit, Millipore, 07-449); and polyclonal anti-H3K4me3 (Rabbit, Active Motif 39159).

EXAMPLE 9

This Example extends the foregoing disclosure and demonstrates that use of four and even three drugs is sufficient to achieve reprogramming of glial cells into neurons. Specifically, this Example demonstrates reprogramming using the combination: SB431542 (TGF-β inhibitor), LDN193189 (BMP inhibitor), CHIR99021 (GSK-3 inhibitor), and DAPT (γ-secretase and Notch inhibitor) to successfully reprogram human glial cells into functional neurons. Further, we have tested each of these four drugs with other drugs combinations that have similar effects and demonstrated that they can all convert human astrocytes into neurons. Thus, the disclosure includes reprogramming glial cells to neurons using combinations of drugs that act on one or a combination of the following signaling pathways: TGF-β, BMP, GSK-3, and γ-secretase/Notch signaling pathways.

The data presented in FIGS. 15-19 show that various drugs with similar activities can be substituted, but still exert the reprogramming effect. Particular combinations demonstrated to be capable of reprogramming include i) LDN193189/CHIR99021/DAPT, ii) SB431542/CHIR99021/DAPT, iii) LDN193189/DAPT/SB431542, and iv) LDN193189/CHIR99021/SB431542. Moreover, we demonstrate that LDN193189 can be replaced by its functional analogues Dorsomorphin, and DMH1; SB431542 can be replaced by Repsox or A8301; CHIR99021 can be replaced by its functional analogues ARA014418 and SB216763, and DAPT can be replaced by its functional analogues BMS906024 and R04929097. Thus, the disclosure demonstrates that any three drug combination from the group SB431542, LDN193189, CHIR99021, and DAPT can reprogram human glial cells into neurons, and any one or more of these can be replaced with a functional analogue and still achieve reprogramming.

While the invention has been described through specific embodiments, routine modifications will be apparent to those skilled in the art and such modifications are intended to be within the scope of the present invention.

What is claimed is:

1. A method for reprogramming human glial cells in the brain of an individual comprising contacting the human glial cells with compounds that collectively inhibit Transforming growth factor beta (TGF-β), Bone morphogenetic protein (BMP), glycogen synthase kinase 3 (GSK-3), and γ-secretase/Notch pathways in the glial cells, wherein the contacting comprises administering to the glial cells in the brain at least one of the following combinations of compounds: i) LDN193189/CHIR99021/N-[(3,5-Difluorophenyl)acetyl]-L-alanyl-2-phenyl]glycine-1,1-dimethylethyl ester (DAPT), ii) SB431542/CHIR99021/DAPT; iii) LDN193189/DAPT/SB431542, or iv)) LDN193189/CHIR99021/SB431542, wherein the administering of the compounds is cell and virus free, and wherein the administering is sufficient such that at least some of the glial cells are reprogrammed to become neurons.

2. A method for generating neurons in the brain of an individual comprising administering to the individual a combination of compounds comprising at least three compounds selected from the group consisting of LDN193189, SB431542, CHIR99021, and N-[(3,5-Difluorophenyl)acetyl]-L-alanyl-2-phenyl]glycine-1,1-dimethylethyl ester (DAPT), wherein the administering of the compounds is cell and virus free, and wherein the neurons are generated.

3. The method of claim 2 wherein the combination of compounds comprises each of LDN193189, SB431542, CHIR99021, and DAPT.

4. The method of claim 1, wherein the combination of the compounds comprises each of LDN193189, SB431542, CHIR99021, and DAPT.

* * * * *